(12) United States Patent
Akhtari et al.

(10) Patent No.: US 8,445,021 B2
(45) Date of Patent: *May 21, 2013

(54) FUNCTIONALIZED MAGNETIC NANOPARTICLES AND METHODS OF USE THEREOF

(75) Inventors: Massoud Akhtari, Pasadena, CA (US); Jerome Engel, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 12/934,044

(22) PCT Filed: Apr. 1, 2009

(86) PCT No.: PCT/US2009/002060
§ 371 (c)(1),
(2), (4) Date: Dec. 21, 2010

(87) PCT Pub. No.: WO2009/123734
PCT Pub. Date: Oct. 8, 2009

(65) Prior Publication Data
US 2011/0110868 A1 May 12, 2011

Related U.S. Application Data

(60) Provisional application No. 61/042,656, filed on Apr. 4, 2008.

(51) Int. Cl.
*A61K 9/14* (2006.01)
(52) U.S. Cl.
USPC .......... 424/489; 424/9.3; 424/490; 424/130.1
(58) Field of Classification Search
USPC ............................. 424/9.3, 130.1, 484, 489
See application file for complete search history.

(56) References Cited

U.S. PATENT DOCUMENTS

| | | | |
|---|---|---|---|
| 5,262,176 A | 11/1993 | Palmacci et al. | |
| 5,612,019 A | 3/1997 | Gordon et al. | |
| 5,622,686 A | 4/1997 | Gordon et al. | |
| 6,548,264 B1 | 4/2003 | Tan et al. | |
| 6,767,635 B1 | 7/2004 | Bahr et al. | |
| 6,797,380 B2 | 9/2004 | Bonitatebus, Jr. et al. | |
| 2004/0146855 A1 | 7/2004 | Marchessault et al. | |
| 2005/0214221 A1 | 9/2005 | Poss et al. | |
| 2005/0260137 A1 | 11/2005 | Acar et al. | |
| 2006/0117397 A1* | 6/2006 | Rutkowski et al. | 800/12 |
| 2006/0142207 A1* | 6/2006 | Tidmarsh et al. | 514/23 |
| 2007/0217998 A1 | 9/2007 | Wong | |
| 2007/0243137 A1 | 10/2007 | Hainfeld | |
| 2008/0206146 A1 | 8/2008 | Akhtari et al. | |

FOREIGN PATENT DOCUMENTS

| | | |
|---|---|---|
| RO | 122439 | 6/2009 |
| WO | WO 03/055379 | 10/2003 |
| WO | 2006/102377 | 9/2006 |
| WO | WO 2006/102377 | 9/2006 |
| WO | WO 2006102377 A2 * | 9/2006 |

OTHER PUBLICATIONS

Berry et al., "Functionalisation of magnetic nanoparticles for applications in biomedicine" *J. Phys. D: Applied Physics*, (2003) 36:R198-R206.
Dousset et al., "Comparison of Ultra small Particles of Iron Oxide (USPIO)—Enhanced T2-Weighted,Conventional T2- Weighted,and Gadolinium-Enhanced T1-Weighted MR Images in Rats with Experimental Autoimmune Encephalomyelitis"*Am. J. Neuroradiol.*, (1999) 20:223-227.
Dousset et al., "In Vivo Macrophage Activity Imaging in the Central Nervous System Detected by Magnetic Resonance" *Magnetic Resonance in Medicine*, (1999) 41:329-333.
Dunning et al., "Superparamagnetic Iron Oxide-Labeled Schwann Cells and Olfactory Ensheathing Cells Can Be Traced InVivo by Magnetic Resonance Imaging and Retain Functional Properties after Transplantation into the CNS" *J. Neurosci.*, (2004) 24:9799-9810.
Moghimi et al., "Long-Circulating andTarget-Specific Nanoparticles:TheorytoPractice" *PharmacoL Rev.*, (2001) 53:283-318.
Pankhurst et al., "Applications of Magnetic nanoparticles in Biomedicine" *J. Phys. D: Applied Physics*, (2003) 36:R167-R181.
Bulent Aydogan et al: "AuNP-DG: Deoxyglucose-Labeled Gold Nanoparticles as X-ray Computed Tomography Contrast Agents for Cancer Imaging", Molecular Imaging and Biology, vol. 12, No. 5, Mar. 17, 2010, pp. 463-467, XP019833379, ISSN: 1860-2002.
Jolesz F A: "Functional imaging of the brain", Medical Instrumentation, vol. 17, No. 1, Jan. 1983-Feb. 1983, pp. 59-62, XP8136772, ISSN: 0090-6689.
Kakizawa Y et al: "Block copolymer-coated calcium phosphate nanoparticles sensing intracellular environment for oligodeoxynucleotide and siRNA delivery", Journal of Controlled Release, vol. 97, No. 2, Jun. 18, 2004, pp. 345-356, XP004515653, ISSN: 0168-3659, DOI: DOI:10.1016/J.JCONREL.2004.03.031.
Sinjan De et al: "Effect of Particle Size of Nanospheres and Microspheres on the Cellular-Association and Cytotoxicity of Paclitaxel in 4T1 Cells", Pharmaceutical Research, vol. 22, No. 5, May 1, 2005, pp. 766-775, XP019370849, ISSN: 1573-904X, DOI: DOI:10.1007/S11095-005-2593-8.

* cited by examiner

*Primary Examiner* — Michael G Hartley
*Assistant Examiner* — Micah-Paul Young
(74) *Attorney, Agent, or Firm* — Paula A. Borden; Bozicevic, Field & Francis LLP.

(57) ABSTRACT

The present disclosure provides compositions comprising 2-deoxyglucose-functionalized magnetic nanoparticles. The compositions are useful in various applications, which are also provided.

32 Claims, 13 Drawing Sheets

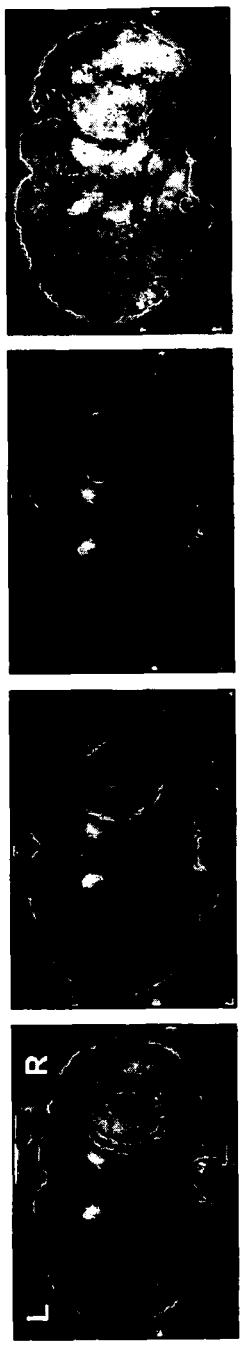

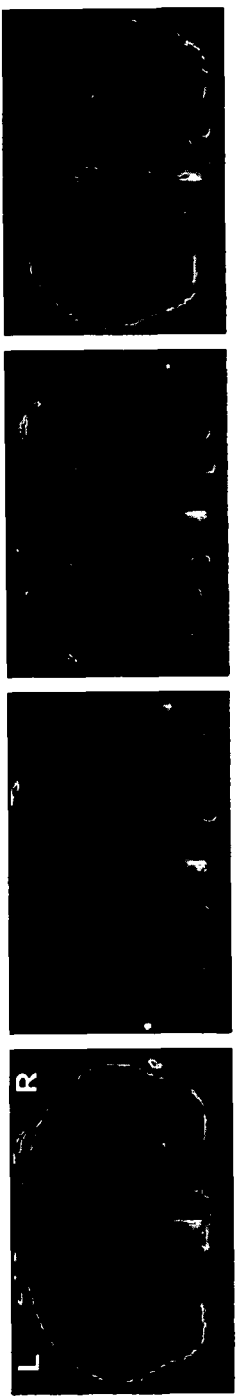

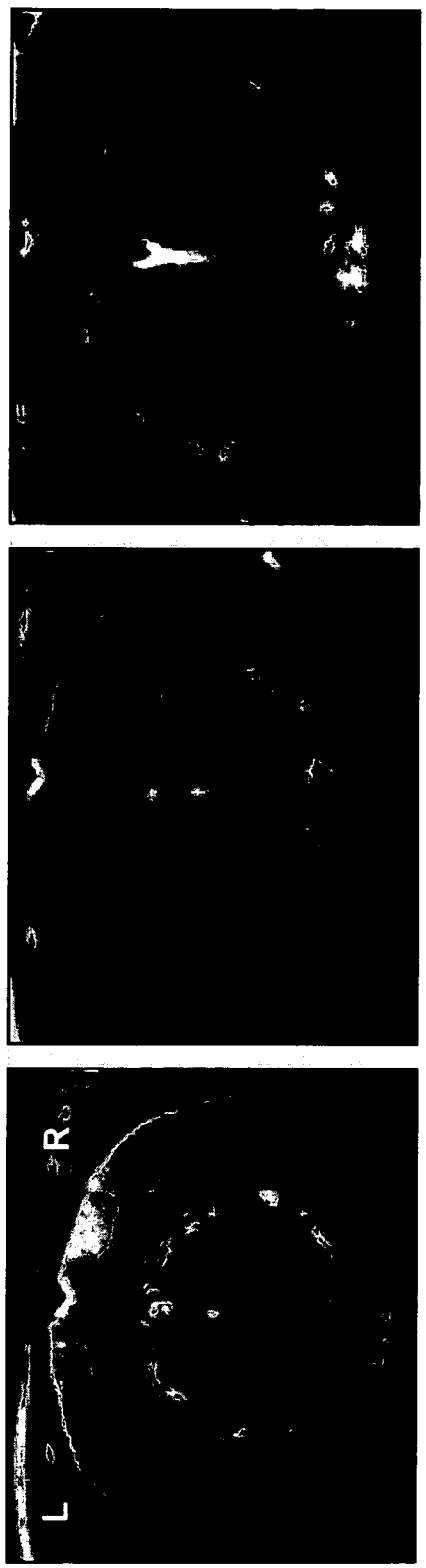

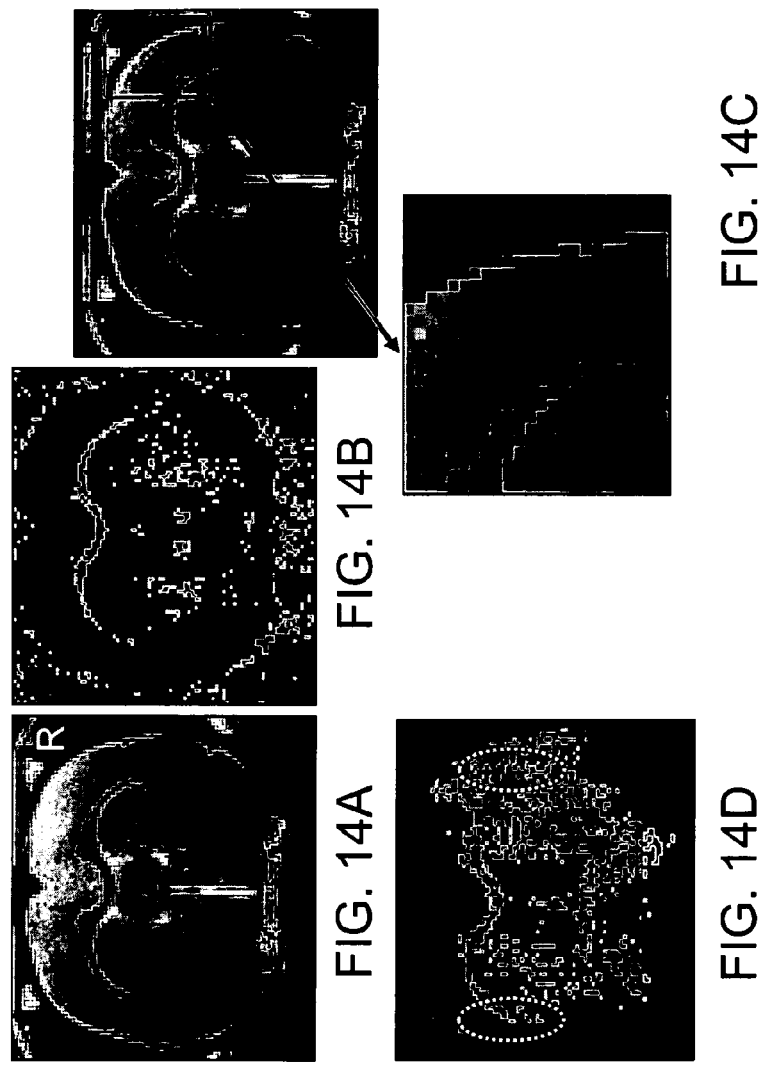

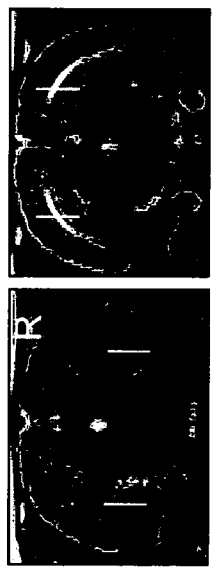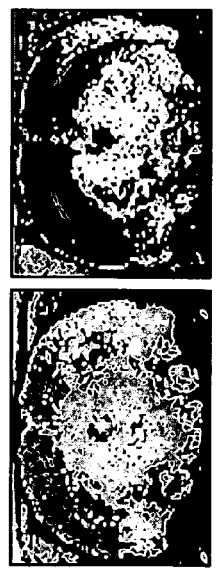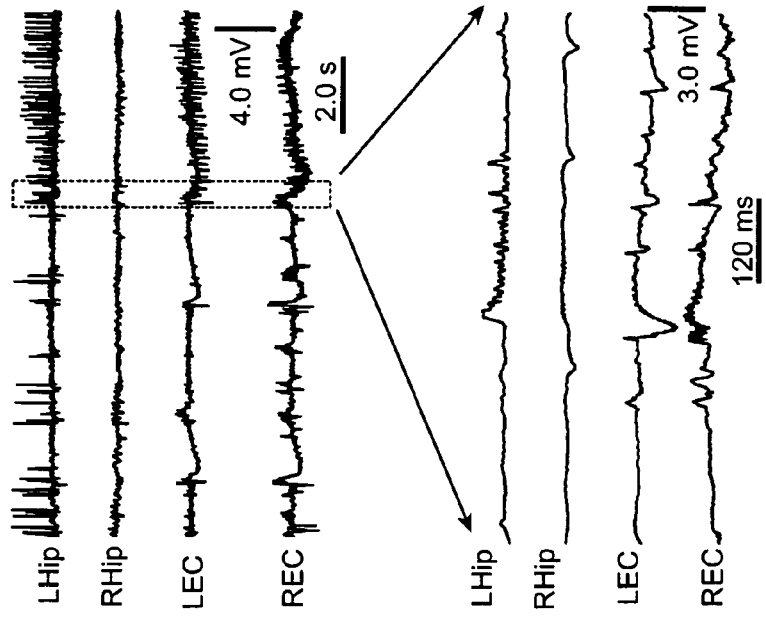

FUNCTIONALIZED MAGNETIC NANOPARTICLES AND METHODS OF USE THEREOF

CROSS-REFERENCE

This application claims the benefit of U.S. Provisional Patent Application No. 61/042,656, filed Apr. 4, 2008, which application is incorporated herein by reference in its entirety.

BACKGROUND

Various imaging techniques are currently in use to diagnose, stage, and monitor various diseases, such as neurological disorders and tumors. Each technique currently in use has certain drawbacks. For example, epileptic regions of activity in the brain are currently localized using electric (electroencephalogram (EEG), electrocorticogram (ECoG), and depth electrode implants), magnetic (magnetoencephalogram (MEG)), and radioactive techniques (positron emission tomography (PET), single photon emission computed tomography (SPECT). EEG and MEG are less sensitive to sources that are more than a few centimeters below the scalp surface and have less sensitivity for detecting epileptic sources of activity that are deeper in the brain parenchyma. The presence of multiple simultaneous sources further confounds quantitative localization due to degeneracy of mathematical solution. In addition, these methods rely on presence of ictal or interictal activity, which may not be present at the time of the testing. ECoG, and depth-implanted electrodes are invasive surgical techniques of considerable cost and health risk, and cause discomfort in patients.

As another example, many primary or metastatic neoplasms cannot be differentiated from normal tissues. PET, PET-computed tomography (PET-CT), and SPECT are used routinely to look for tumor activity so as to grade tumors. PET and SPECT involve administration of radioactive substances. PET traces have short half-life times, are not widely available, and are limited in their usefulness as diagnostic techniques.

There is a need in the art for diagnostic tracers and methods that avoid one or more of the above-mentioned drawbacks.

Literature

U.S. Pat. Nos. 6,548,264, 6,767,635; Berry and Curtis (2003) *J. Phys. D: Applied Physics* 36:R198-R206; Pankhurst et al. (2003) *J. Phys. D: Applied Physics* 36:R167-R181; Dousset et al. (1999) *Am. J. Neuroradiol.* 20:223-227; Dunning et al. (2004) *J. Neurosci.* 24:9799-9810; Dousset et al. (1999) *Magnetic Resonance in Medicine* 41:329-333; Moghimi et al. (2001) *Pharmacol. Rev.* 53:283-318; U.S. Pat. Nos 5,262,176; 6,797,380; US 2005/0260137; US 2007/0217998; US 2005/0214221; US 2004/0146855; WO 03/055379; U.S. Pat. Nos. 5,622,686; 5,612,019; WO 2006/102377; US 2008/0206146.

SUMMARY OF THE INVENTION

The present disclosure provides compositions comprising 2-deoxyglucose-functionalized magnetic nanoparticles. The compositions are useful in various applications, which are also provided.

BRIEF DESCRIPTION OF THE DRAWINGS

FIGS. 1A-D depict results of tumor studies with 2DG-MNP.

FIGS. 2A-D show 2DG-MNP contrast enhancement in a resting mouse brain.

FIGS. 5A-C show 2DG-MNP contrast enhancement produced in a chronic kainic acid-treated animal in the interictal period.

FIGS. 14A-D depict images of a naïve rat brain, and rat brain after electrical stimulation of the left forepaw.

FIGS. 15A-E depict images of rat brain activity before and after induced seizures.

DEFINITIONS

Figure 3C:
FIGS. 3A-E depict results of studies of pentylene tetrazole-induced acute epilepsy, using 2DG-MNP, and comparison with $^{14}$C-2DG autoradiography (PET).

As used herein, the term "nanoparticle" refers to a particle having a diameter of between about 1 and 1000 nm. Similarly, the term "nanoparticles" refers to a plurality of particles having an average diameter of between about 1 and 1000 nm.

Reference to the "size" of a nanoparticle is a reference to the length of the largest straight dimension of the nanoparticle. For example, the size of a perfectly spherical nanoparticle is its diameter.

As used herein, the term "functional group," used interchangeably with "functional moiety" and "functional ligand," refers to a chemical group that imparts a particular function to a magnetic nanoparticle bearing the chemical group. For example, functional groups can include macromolecular substances such as antibodies, oligonucleotides, carbohydrates, biotin, or streptavidin, polypeptides (including polypeptides that comprise non-amino acid moieties such as phosphate groups, sugars, carbohydrates, lipids, etc.), and hormones. Functional groups can include macromolecular substances that are known to bind particular molecules, where such macromolecular substances are members of specific binding pairs. Functional groups can include small chemical groups comprising moieties such as amines, amides, pyridinium, quinazolines, heterocyclic groups, aryl groups, carboxylates, and the like. Functional groups can comprise a radioactive moiety. For example, a functional group includes any of the foregoing groups, where the group is radioactive.

As used herein, the terms "subject," "individual," "host," and "patient" refer interchangeably to any subject for whom diagnosis, prognosis, or therapy is desired, and generally refers to the recipient of a diagnostic method, a prognostic method, or a therapeutic method, to be practiced according to the invention. Suitable subjects include vertebrates, e.g., mammals. Suitable mammalian subjects include, but are not limited to, humans, non-human primates, rodents (e.g., rats, mice), ungulates (e.g., bovines, ovines, porcines, equines, etc.), felines, and canines.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

As used herein, the terms "differential binding" or "selective binding," in the context of differential binding or selective binding of a functionalized MNP to a particular tissue, refer to binding of a functionalized MNP to a first tissue in such a manner that the binding to the first tissue is distinguishable from binding (if any) of the functionalized MNP to a second tissue. For example, in some embodiments, a subject functionalized MNP binds to a diseased tissue in such a manner that the binding of the functionalized MNP to the diseased tissue is distinguishable from binding (if any) of the functionalized MNP to a non-diseased tissue.

As used herein, the term "differential affinity" of a functionalized MNP for a particular tissue refers to binding of a functionalized MNP to the particular tissue with an affinity that is at least about 10%, at least 25%, at least about 50%, at least about 100% (or 2-fold), at least about 2.5-fold, at least about 5-fold, at least about 10-fold, at least about 50-fold, at least about $10^2$-fold, at least about $5 \times 10^2$-fold, at least about $10^3$-fold, at least about $5 \times 10^3$-fold, at least about $10^4$-fold, at least about $5 \times 10^4$-fold, at least about $10^5$-fold, or more, higher than the binding of the functionalized MNP to a second tissue. Differential affinity of a functionalized MNP can provide for differential binding or selective binding of the functionalized MNP to a particular tissue.

As used herein, the term "differential metabolic uptake" of a functionalized MNP into a particular tissue or cell refers to metabolic uptake of a functionalized MNP into a first tissue or a first cell in a manner that is distinguishable from the metabolic uptake of the functionalized MNP into a second tissue or a second cell. For example, in some embodiments, a functionalized MNP exhibits differential metabolic uptake into a diseased tissue in a manner that is distinguishable from the metabolic uptake (if any) of the functionalized MNP into a normal (non-diseased) tissue. As another example, in some embodiments, a functionalized MNP exhibits differential metabolic uptake into a cancer cell in a manner that is distinguishable from the metabolic uptake (if any) of the functionalized MNP into normal (non-cancerous) cell of the same cell type.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, e.g., in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a functionalized magnetic nanoparticle" includes a plurality of such nanoparticles and reference to "the functional moiety" includes reference to one or more functional moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions comprising 2-deoxyglucose-functionalized magnetic nanoparticles (2-DG-functionalized MNPs, or 2DG-MNPs). A subject composition is useful in diagnostic (e.g., imaging) methods, which methods are provided. A subject composition can also be used in treatment methods, as described below.

Compositions

The present disclosure provides functionalized magnetic nanoparticles (MNPs) that comprises a least one functional moiety, e.g., comprising at least 2-deoxyglucose (2DG). In some embodiments, a subject functionalized MNP comprises only 2-DG as a functional moiety. In other embodiments, a subject functionalized MNP comprises, in addition to 2DG, at least a second functional moiety. The term "2DG-functionalized MNP" includes a functionalized MNP that comprises only 2DG as a functional moiety and a functionalized MNP that comprises, in addition to 2DG, at least a second functional moiety, e.g., one or more additional functional moieties.

A subject functionalized MNP comprises an MNP and one or more functional groups, where the one or more functional groups includes at least 2DG. The MNP comprises a magnetic core particle and a biocompatible substrate. The one or more functional groups is linked to the biocompatible substrate, either directly or via a linker. The combination of the biocompatible substrate and the one or more functional groups is referred to herein as the "coating."

Suitable biocompatible substrates include, but are not limited to, polysaccharides and oligosaccharides, and derivatives thereof, including, e.g., dextran, an iron-dextran complex, carboxymethyl dextran, starch, dialdehyde starch, chitin, alginate, cellulose, and carboxymethylcellulose; a polymer, including e.g., a polyethylene glycol, a polyethylene oxide, a poloxamer, a poloxamine, polystyrene, polyethylene, polyvinyl chloride, polyvinylpyrrolidone, polyethyleneimine, a polymethylacrylate, a polyvinyl alcohol, and an acrylic polymer; a phospholipid; a compound such as silica, aluminum silica, a silicone, etc.; and proteins and derivatives thereof, including, e.g., albumin, synthetic proteins, etc.

A subject 2DG-functionalized MNP (a "2DG-MNP") exhibits differential affinity for and/or metabolic uptake into a mammalian tissue. In some embodiments, the mammalian tissue is human tissue. In other embodiments, the mammalian tissue is a non-human primate tissue. In other embodiments, the mammalian tissue is a rodent (e.g., mouse, rat, etc.) tissue. In other embodiments, the mammalian tissue is a tissue of a canine, a feline, an ungulate (e.g., an equine, a bovine, an ovine, and the like), or other non-human mammal. A subject 2DG-functionalized MNP allows imaging of a tissue in a living individual, e.g., a living mammal (e.g., a living rodent, a living human, a living non-human primate, a living ungulate, a living canine, a living feline, etc.). A subject 2DG-functionalized MNP allows imaging of a tissue in a living individual without the need for radioactivity. Thus, in some embodiments, a subject 2DG-MNP does not comprises any radioactive moieties. A subject 2DG-MNP can include a radioactive moiety, but in many embodiments will not include any radioactive moiety.

In some embodiments, a subject 2DG-functionalized MNP exhibits differential affinity for a particular mammalian tissue. In some embodiments, a subject 2DG-functionalized MNP exhibits differential affinity for a diseased mammalian tissue, e.g., a subject 2DG-functionalized MNP exhibits an affinity for a diseased tissue that is at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the 2DG-functionalized MNP for a non-diseased tissue, e.g., for a non-diseased tissue of the same tissue type. For example, in some embodiments, a subject 2DG-functionalized MNP exhibits differential affinity for an epileptic brain tissue, e.g., a subject 2DG-functionalized MNP exhibits an affinity for an epileptic brain tissue that is at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the 2DG-functionalized MNP for a non-epileptic brain tissue, e.g., for a non-epileptic brain tissue of the same brain region as the epileptic brain tissue.

In some embodiments, a subject 2DG-functionalized MNP exhibits differential metabolic uptake into a particular mammalian cell and/or tissue. In some embodiments, a subject 2DG-functionalized MNP exhibits differential metabolic uptake into a diseased mammalian tissue, e.g., a subject 2DG-functionalized MNP exhibits an at least about 1%, at least about 5%, at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, greater metabolic uptake into the diseased tissue, compared to the metabolic uptake of the 2DG-functionalized MNP into a non-diseased tissue, e.g., a non-diseased tissue of the same tissue type. For example, in some embodiments, a subject 2DG-functionalized MNP exhibits differential metabolic uptake into a cancerous mammalian tissue such as a tumor, e.g., a subject 2DG-functionalized MNP exhibits an at least about 1%, at least about 5%, at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, greater metabolic uptake into the cancerous tissue (e.g., the tumor), compared to the metabolic uptake of the 2DG-functionalized MNP into a non-cancerous tissue, e.g., a non-cancerous tissue of the same tissue type, or compared to the metabolic uptake of the 2DG-MPN into normal, non-cancerous tissue adjacent to or surrounding a tumor. Whether a 2DG-functionalized MNP exhibits differential metabolic uptake into a particular mammalian cell and/or tissue can be determined, e.g., using magnetic resonance imaging (MRI) or computed tomography (CT). A signal intensity change over time with repeated data acquisitions is observed when a functionalized MNP exhibits differential metabolic uptake into a cell and/or tissue.

Diseased tissues that can be detected using a subject 2DG-functionalized MNP include, but are not limited to, a neoplasm; epileptogenic tissues or a tissue affected by epileptic activities; a plaque associated with Alzheimer's Disease; a tissue affected by Huntington's Disease; a tissue affected by Parkinson's Disease; a diseased cardiac tissue; a tissue exhibiting or affected by amyotrophic lateral sclerosis; a tissue exhibiting or affected by an acute inflammatory disease; a tissue exhibiting or affected by a chronic inflammatory disease; a tissue exhibiting or affected by an infectious disease (e.g., an infected tissue); a diseased vascular tissue; a diseased gastro-intestinal tissue; diseased bone or bone marrow tissue; a diseased kidney tissue; a diseased muscle tissue; a diseased fatty tissue; a brain tissue affected by a psychological, cognitive, or psychiatric disorder, e.g., a brain tissue affected by autism, depression, addiction, or schizophrenia; a diseased pancreatic tissue; a diseased central nervous system tissue; and the like. In some embodiments, the disease tissue is a tumor. In some embodiments, the diseased tissue is an epileptogenic tissue (e.g., an epileptogenic brain tissue) or a tissue affected by epileptic activities.

Magnetic Nanoparticles

Subject nanoparticles generally have a mean size in a range of from about 1 nm to about 1500 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1500 nm. Average diameters will in some embodiments range from about 10 nm to about 1500 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, from about 800 nm to about 1000 nm, or from about 1000 nm to about 1500 nm. This size refers to the magnetic core particle plus the coating (e.g., biocompatible substrate plus one or more functional moieties).

The magnetic core particle can have a diameter of from about 1 nm to about 1000 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, or from about 800 nm to about 1000 nm.

The coating can have a thickness (e.g., the average distance from the outside surface of the core magnetic particle to the outside surface of the coating) of from about 1 nm to about 500 nm, e.g., from about 1 nm to about 5 nm, from about 5 nm to about 10 nm, from about 10 nm to about 15 nm, from about 15 nm to about 20 nm, from about 20 nm to about 25 nm, from about 25 nm to about 30 nm, from about 30 nm to about 40 nm, from about 40 nm to about 50 nm, from about 50 nm to about 60 nm, from about 60 nm to about 70 nm, from about 70 nm to about 80 nm, from about 80 nm to about 90 nm, from about 90 nm to about 100 nm, from about 100 nm to about 125 nm, from about 125 nm to about 150 nm, from about 150 nm to about 175 nm, from about 175 nm to about 200 nm, from about 200 nm to about 225 nm, from about 225 nm to about 250 nm, from about 250 nm to about 275 nm, from about 275 nm to about 300 nm.

The ratio of the thickness of the coating to the diameter of the magnetic core particle is from about 1:1 to about 1:1000, e.g., from about 1:1 to about 1:1.5, from about 1:1.5 to about 1:2, from about 1:2 to about 1:2.5, from about 1:2.5 to about 1:5, from about 1:5 to about 1:10, from about 1:10 to about 1:25, from about 1:25 to about 1:50, from about 1:50 to about 1:100, from about 1:100 to about 1:250, from about 1:250 to about 1:500, from about 1:500 to about 1:750, or from about 1:750 to about 1:1000.

The diameter of the magnetic core of a subject functionalized MNP can be from about 1% to about 99% of the diameter of the entire functionalized MNP, e.g., the diameter of the magnetic core of a subject functionalized MNP can be from about 1% to about 5%, from about 5% to about 10%, from about 10% to about 25%, from about 25% to about 50%, from about 50% to about 75%, or from about 75% to about 99% of the diameter of the entire functionalized MNP.

The weight of the magnetic core of a subject functionalized MNP can be from about 1% to about 99% of the weight of the entire functionalized MNP, e.g., the weight of the magnetic core of a subject functionalized MNP can be from about 1% to about 5%, from about 5% to about 10%, from about 10% to about 25%, from about 25% to about 50%, from about 50% to about 75%, or from about 75% to about 99% of the weight of the entire functionalized MNP.

One or more properties of a subject functionalized MNP can vary, depending on the ratio of the diameter of the magnetic core to the diameter of the entire functionalized MNP. Such properties include, e.g., blood circulation time, resonance heating properties, transport across various tissues, transport across an endothelial cell layer, transport across the blood-brain barrier, particle clearance time, particle metabolism time, exposure of the core particle, MRI enhancement properties such as effect on T1, T2, T2*, effect on relaxation times of the particle in an externally applied magnetic field, and the like.

Nanoparticles can be simple aggregations of molecules or they can be structured into two or more layers of different substances. For example, simple nanoparticles consisting of magnetite or maghemite are suitable for use. See, e.g., Scientific and Clinical Applications of Magnetic Microspheres, U. Hafeli, W. Schutt, J. Teller, and M. Zborowski (eds). Plenum Press, New York, 1997; and Tiefenauer et al., Bioconjugate Chem. 4:347, 1993. More complex nanoparticles can consist of a core made of one substance and one or more shells made of another substance(s). The term "magnetic nanoparticle" includes paramagnetic nanoparticles, diamagnetic nanoparticles, and ferromagnetic nanoparticles.

Exemplary core materials that are suitable for inclusion in a subject functionalized MNP include ferrites of general composition $MeO_xFe_2O_3$ wherein Me is a bivalent metal such as Co, Mn or Fe. Other suitable materials are $\gamma$-$Fe_2O_3$, the pure metals Co, Fe, Ni, and metal compounds such as carbides and nitrides. The core material is generally an MRI visible agent. The core material is typically coated. Suitable coatings include, but are not limited to, dextran, albumin, starch, silicon, and the like.

Many different type of small particles (nanoparticles or micron-sized particles) are commercially available from several different manufacturers including: Bangs Laboratories (Fishers, Ind.); Promega (Madison, Wis.); Dynal Inc. (Lake Success, N.Y.); Advanced Magnetics Inc. (Surrey, U.K.); CPG Inc. (Lincoln Park, N.J.); Cortex Biochem (San Leandro, Calif.); European Institute of Science (Lund, Sweden); Ferrofluidics Corp. (Nashua, N.H.); FeRx Inc.; (San Diego, Calif.); Immunicon Corp.; (Huntingdon Valley, Pa.); Magnetically Delivered Therapeutics Inc. (San Diego, Calif.); Miltenyi Biotec GmbH (USA); Microcaps GmbH (Rostock, Germany); PolyMicrospheres Inc. (Indianapolis, Ind.); Scigen Ltd. (Kent, U.K.); Seradyn Inc.; (Indianapolis, Ind.); and Spherotech Inc. (Libertyville, Ill.). Such particles can be made using conventional techniques, such as grinding and milling, emulsion polymerization, block copolymerization, and microemulsion.

Methods of making silica nanoparticles have also been reported. The processes involve crystallite core aggregation (Philipse et al., Langmuir, 10:92, 1994); fortification of superparamagnetic polymer nanoparticles with intercalated silica (Gruttner, C and J Teller, Journal of Magnetism and Magnetic Materials, 194:8, 1999); and microwave-mediated self-assembly (Correa-Duarte et al., Langmuir, 14:6430, 1998).

The core of a subject functionalized MNP is magnetic and can include a metal selected from the group consisting of magnetite, maghemite, and greigite. Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies.

In some embodiments, the core includes a pigment which can be an inorganic salt such as potassium permanganate, potassium dichromate, nickel sulfate, cobaltchloride, iron (III) chloride, or copper nitrate. Similarly, the core can include a dye such as Ru/Bpy, Eu/Bpy, or the like; or a metal such as Au, Ag, and Cd.

In some embodiments, the core includes a component selected from graphite, a graphite derivative, a carbon compound, a metal carbide, silicon carbide, and the like. For example, in some embodiments, the core includes maghemite, and a component selected from graphite, a graphite derivative, a carbon compound, a metal carbide, silicon carbide, and the like.

In some embodiments, a subject functionalized nanoparticle comprises a core and a silica shell enveloping the core. A functional group is conjugated to the silica shell, e.g., as described in U.S. Pat. No. 6,548,264. Numerous known methods for attaching functional groups to silica can be adapted for use in the present disclosure. See, e.g., Ralph K. Iler, The Chemistry of Silica: Solubility, Polymerization, Colloid and Surface Properties, and Biochemistry, Wiley-Interscience, NY, 1979; VanDerVoort, P. and Vansant, E. F., Journal of Liquid Chromatography and Related Technologies, 19:2723-2752, 1996; and Immobilized Enzymes. Antigens, Antibodies, and Peptides: Preparation and Characterization, Howard H. Weetall (ed.), M. Dekker, NY, 1975. An exemplary process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. Antibodies or other proteins can then be covalently coupled to the silanized surface using the cyanogen bromide (CNBr) method. As one example, CNBr-mediated coupling can be achieved by suspending silica-coated nanoparticles previously silanized with DETA in a 2 M sodium carbonate buffer and ultrasonicating the mixture to create a particle suspension. A solution of CNBr (e.g., 2 g CNBr/1 ml acetonitirile) is then added to the particle suspension to activate the nanoparticles. After washing the nanoparticles with a neutral buffer (e.g., phosphate buffered saline, pH 8), an antibody solution is added to the activated nanoparticle suspension causing the antibodies to become bound to the nanoparticles. A glycine solution can also be added to the antibody-coated nanoparticles to block any remaining unreacted sites.

In some embodiments, the magnetic nanoparticle is dextran coated. Magnetic nanoparticles are made using any known process. For example, magnetic iron-dextran particles can be prepared by mixing 10 ml of 50% (w/w) aqueous Dextran T-40 (Pharmacia) with an equal volume of an aqueous solution containing 1.51 g $FeCl_3$-$6H_2O$ and 0.64 g $FeCl_2$-$4H_2O$. While stirring, the mixture is titrated to pH 10-11 by the drop-wise addition of 7.5% (v/v) $NH_4OH$ heated to 60-65° C. in a water bath for 15 minutes. Aggregates are then removed by 3 cycles of centrifugation in a low-speed clinical centrifuge at 600×g for 5 minutes. The ferromagnetic iron-dextran particles are separated from unbound dextran by gel filtration chromatography on Sephacryl-300. Five ml of the reaction mixture is then applied to a 2.5×33 cm column and eluted with 0.1 M sodium acetate and 0.15 M NaCl at pH 6.5. The purified ferromagnetic iron-dextran particles collected in the void volume will have a concentration of 7-10 mg/ml as determined by dry weight analysis. Molday and Mackenzie (1982) Journal of Immunological Methods 52:353-367. Also see (Xianqiao (2003) China Particuology Vol. 1, No. 2, 76-79).

In some embodiments, a subject functionalized magnetic nanoparticle is of the formula: M-(L)-Z, the linkage sites between L and Z having covalently bound functional groups, wherein M represents the magnetic core particle, L represents an optional linker group, and Z represents a functional group. In other embodiments, a subject functionalized magnetic nanoparticle is of the formula: M-S-(L)-Z, the linkage sites between S and L and L and Z having covalently bound functional groups, wherein M represents the magnetic core particle, wherein S represents a biocompatible substrate fixed to M, wherein M represents the magnetic core particle, L represents an optional linker group, and Z represents a functional group. In some embodiments, a subject functionalized magnetic nanoparticle is of the formula: M-(L)-Z, where M represents the magnetic core particle, where L represents an optional linker group, and where Z represents a functional group. In other embodiments, a subject functionalized magnetic nanoparticle is of the formula: M-S-(L)-Z, where M represents the magnetic core particle, where S represents a biocompatible substrate surrounding M or attached to M, where L represents an optional linker group, and where Z represents a functional group. Functional groups include moieties that provide for binding to a specific tissue type or cell type; moieties that provide for crossing the blood-brain barrier (BBB); therapeutic agents; and the like.

In some embodiments, a subject functionalized magnetic nanoparticle comprises two or more different functional groups attached to the same core particle or to the same biocompatible substrate surrounding or attached to the core particle. For example, in some embodiments, a subject functionalized magnetic nanoparticle is of the formula M-(L)-$Z_1Z_2$, or M-S-(L)-$Z_1Z_2$, where $Z_1$ and $Z_2$ are different functional groups, where M is a magnetic core particle, and where L, if present, is a linker. In some embodiments, for example, $Z_1$ is a 2DG moiety and $Z_2$ is a therapeutic agent. In other embodiments, for example, $Z_1$ is a 2DG moiety, and $Z_2$ is a cell type-specific binding moiety. In other embodiments, for example, $Z_1$ is a 2DG moiety; and $Z_2$ is a moiety that provides for crossing the blood-brain barrier (BBB). In some embodiments, a subject functionalized magnetic nanoparticle is of the formula M-S-(L)-$Z_1Z_2$, where M is a magnetic core particle, where the moieties $Z_1$ and $Z_2$ are each linked to the substrate (S), either directly or via a linker (L) (e.g., L, if present, is a linker). In some embodiments, a subject functionalized magnetic nanoparticle comprises at least a third functional moiety $Z_3$. Thus, e.g., in some embodiments, a subject functionalized magnetic nanoparticle is of the formula M-S-(L)-$Z_1Z_2Z_3$, where the moieties $Z_1$, $Z_2$, and $Z_3$ are each linked to the substrate, either directly or via a linker. In some embodiments, $Z_1$ is a 2DG moiety; $Z_2$ is a first therapeutic agent; and $Z_3$ is a second therapeutic agent. In other embodiments, $Z_1$ is a 2DG moiety; $Z_2$ is a therapeutic agent; and $Z_3$ is a moiety that provides for crossing the BBB.

In some embodiments, the magnetic core particles consist of magnetite, maghemite, ferrites of general formula $MeO_xFe_2O_3$ wherein Me is a bivalent metal such as cobalt, gold, manganese, iron, or of cobalt, iron, nickel, iron carbide, or iron nitride, as described above. If present, the substrate S is a biocompatible substrate comprising one or more compounds such as polysaccharides or oligosaccharides or derivatives thereof, such as dextran, carboxymethyldextran, starch, dialdehyde starch, chitin, alginate, cellulose, carboxymethylcellulose; proteins or derivatives thereof, such as albumins, peptides, synthetic polypeptides, and polypeptides modified with a non-amino acid group such as a sugar, a lipid, a polysaccharide, a phosphate group, etc.; synthetic polymers, such as polyethyleneglycols, polyvinylpyrrolidone, polyethyleneimine, polymethacrylates, bifunctional carboxylic acids and derivatives thereof, such as mercaptosuccinic acid or hydroxycarboxylic acids; and radioactive versions of any of the foregoing.

The linker group L can be formed by reaction of a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups; or radioactive versions of any of the foregoing.

In some embodiments, a subject functionalized magnetic nanoparticle is capable of passing the blood-brain barrier. For example, a subject functionalized magnetic nanoparticle may comprise, attached to the nanoparticle, or in a formulation with the nanoparticle, or coating the nanoparticle, one or more polymers. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, a subject functionalized magnetic nanoparticle is coated with a polysorbate such as, e.g., Tween® 80 (which is Polyoxyethylene-80-sorbitan monooleate), Tween® 40 (which is Polyoxyethylene sorbitan monopalmitate); Tween® 60 (which is Polyoxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly (vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923, 986. Other methods for crossing the blood brain barrier are discussed in various publications, including, e.g., Chen et al. (2004) Curr. Drug Delivery 1:361-376.

In some embodiments, a subject functionalized MNP comprises one or more agents that provide for evasion of the reticuloendothelial system (RES). Agents that provide for evasion of the RES include, but are not limited to, a block copolymer non-ionic surfactant such as a poloxamine, such as poloxamine 508, poloxamine 908, poloxamine 1508, etc. For poloxamines, see, e.g., Moghimi and Hunter (2000) Trends Biotechnol. 18:412. In some embodiments, a subject functionalized MNP comprises about 1% poloxamine. Poloxamines are polyoxyethylene, polyoxypropylene block copolymers of ethylene diamine.

Nanoparticles can also be transferred across the BBB by utilizing the specific delivery channels that are present in the BBB. As one non-limiting example, attachment of alpha-methyl tryptophan to the nanoparticles renders the tryptophan channels receptive to these particles and aids in delivery across the BBB. Other mechanisms are transcytosis and diapedesis, with or without the mediation of the channels present at the BBB.

Generating 2DG

As used herein, "2DG" includes 2DG derivatives and 2DG variants. 2-Deoxyglucose (2-DG) is also called 2-deoxy-D-glucose, 2-deoxy-D-arabino-hexose, or D-arabino-2-deoxy-hexose. 2DG is a component of anticancer drugs such as daunomycin, adriamycin, carminomycins, and antibiotics with a lactonic ring. 2DG derivatives and variants include, but are not limited to, all therapeutic or functional molecules that contain one or more 2DG molecule(s) its derivatives or variants as part of their basic chemical structure.

Production of 2DG can be carried out using any known method. For example, 2-DG can be prepared from various starting materials such as D-glucose, D-mannose, calcium D-gluconate, D-arabinose, D-glucosamine hydrochloride, N-acetyl glucosamine, chitin, and chitosan and carboxymethylchitosan. Preparation methods vary with various starting materials. For example, D-glucose can be methylated and brominated, followed by debromination and acid hydrolysis to yield β-2DG. Bergmann et. al. (1992) Berichte der Deutschen Chemischen Gesellschaft Jahrg. 55:158-72. D-glucose or D-mannose can be treated with bromine and acetyl, followed by a Fischer procedure (Fischer et al. (1914) (Berichte der Deutschen Chemischen Gesellschaft Jahrg. 47:196-210), to yield 3,4,6-tri-O-acetyl-1,5-anhydro-2-deoxy-D-arabino-hex-1-enitol, which is reacted with bromine, then reduced to remove the acetyl group, yielding 2DG (Arita et al. (1972) Bull. Chem. Soc. Japan 45:567-69). The 3,4,6-tri-O-acetyl-1,5-anhydro-2-deoxy-D-arabino-hex-1-enitol intermediate can be treated with N-bromosuccinimide, followed by hydrogenation and deacetylation to yield 2DG. Monneret and Choay (1981) Carbohydr. Res. 96:299-305. D-glucose can be reacted with ethanethiol and benzoyl chloride, followed by dehydrogenation, reduction, and deprotection to give 2-DG. Wong and Gray (1980) Carbohydr. Res. 80:87-98). Glucal can be deacetylated by reacting with sulfuric acid to give 2-DG with an overall yield of 35%. Overend et al. (1949) J. Chem. Soc., 1:2841-45. D-arabinose can be treated with nitromethane and an acetylating agent, followed by treatment with diluted sodium hydroxide, to yield a-2-DG. Sowden and Fischer (1947)J. Am. Chem. Soc. 69:1048-50. D-arabinose can be condensed, reduced with acetone, then reacted with trifluoromethanesulfonic anhydride, to yield a product that is then reacted with sodium cyanide, followed by hydrogenation, reduction, and hydrolysis, yielding 2-DG. Shiue et al. (1979) Carbohydr. Res. 74:323-26.

D-arabinose is also a rare natural single sugar, but can be made by oxidizing and removing carboxyl from D-glucose acidic calcium. In addition, 2DG can be derived by removing the amino group from glucosaminol, aminoglucoside, or aminosaccharide, using hydroxylamino-O-Sulfonic acid (HOS).

Chitin and chitosan can also be used to produce poly 2DG fiber. After removing the amino group from chitin or chitosan with HOS, carboxymethyl chitosan produces poly(carboxymethyl) 2DG. Matsushima (1951) Bull. Chem. Soc. Japan 24:144-47; and Bando and Matsushima (1973) Bull. Chem. Soc. Japan 46:593-96.

Aspinall et al. ((1980) Carbohydr. Res. 78:275-83) describe treating N-acetyl-D-glucosamine with hydrogenation, then with hydrazine sulfate, followed by removal of the amino group using nitrous acid, to get 2DG, in which the yield of 2-deoxy-D-glucose is 44.4%.

Amarp et al. ((1980) Carbohydr. Res. 78:394-97) reacted alpha and beta D-methyl-glucosamineside HCl with HOS, and produced corresponding alpha and β-2DG and β-2 deoxy-methyl-glucoside, where the yields were 55% and 31%, respectively.

Coupling 2DG to an MNP

As noted above, a subject functionalized MNP comprises an MNP and one or more functional moieties, where a subject functionalized MNP comprises 2DG and, in some embodiments, at least a second functional moiety. In some embodiments, a subject functionalized MNP includes a magnetic core particle, a biocompatible substrate, and at least one functional moiety coupled directly or via a linker to the biocompatible substrate. For example, 2DG is linked to the biocompatible substrate, either directly or via a linker.

In some embodiments, the 2DG is linked to the biocompatible substrate of the MNP via the oxygen atom of a hydroxyl group on the 2DG. Thus, e.g., in some embodiments, the 2DG is linked to the biocompatible substrate, directly or via a linker, via the 1-OH, the 3-OH, the 4-OH, or the 6-OH oxygen of the 2DG. In some embodiments, the 2DG is linked to the biocompatible substrate, directly or via a linker, via the 1-OH oxygen of the 2DG. In some embodiments, the 2DG is linked to the biocompatible substrate, directly or via a linker, via the 3-OH oxygen of the 2DG. In some embodiments, the 2DG is linked to the biocompatible substrate, directly or via a linker, via the 4-OH oxygen of the 2DG. In some embodiments, the 2DG is linked to the biocompatible substrate, directly or via a linker, via the 6-OH oxygen of the 2DG.

In some embodiments, depending on the site of the linkage on the 2DG to the biocompatible substrate, the 2DG-functionalized MNP will exhibit differential affinity and/or metabolic uptake into different tissue and/or cell types.

In other embodiments, the 2DG is linked to the biocompatible substrate of the MNP via a carbon atom of the 2DG. Thus, e.g., in some embodiments, the 2DG is linked, directly or via a linker, to the biocompatible substrate, via one of $C_{1-6}$ of the 2DG. In some embodiments, the 2DG is linked, directly or via a linker, to the biocompatible substrate, via $C_1$ of the 2DG. In some embodiments, the 2DG is linked, directly or via a linker, to the biocompatible substrate, via $C_2$ of the 2DG. In some embodiments, the 2DG is linked, directly or via a linker, to the biocompatible substrate, via $C_3$ of the 2DG. In some embodiments, the 2DG is linked, directly or via a linker, to the biocompatible substrate, via $C_4$ of the 2DG. In some embodiments, the 2DG is linked, directly or via a linker, to the biocompatible substrate, via $C_5$ of the 2DG. In some embodiments, the 2DG is linked, directly or via a linker, to the biocompatible substrate, via $C_6$ of the 2DG.

Additional Functional Moieties

As noted above, in some embodiments, a subject 2DG-functionalized MNP will further include at least a second functional moiety.

Suitable at least second functional moieties include, but are not limited to, therapeutic agents;

targeting moieties (e.g., moieties that provide for targeting to a particular cell type or tissue type; agents that provide for detection, e.g., dyes; agents that provide for crossing the blood-brain barrier; and the like.

Therapeutic Agents

In some embodiments, the at least second functional moiety is a therapeutic agent, e.g., for delivery to a diseased tissue. The nature of the therapeutic agent will depend, in part, on the condition or pathology being treated. For example, where the disorder is epilepsy, suitable therapeutic agents include, but are not limited to, anti-seizure agents. Where the disorder is a brain tumor, suitable therapeutic agents include, but are not limited to, anti-neoplastic agents. Where the disorder is an inflammatory condition of vascular tissue or bone tissue, suitable therapeutic agents include, but are not limited to, anti-inflammatory agents.

Suitable therapeutic agents include, but are not limited to, drugs acting at synaptic and neuroeffector junctional sites; general and local analgesics and anesthetics such as opioid analgesics and antagonists; hypnotics and sedatives; drugs for the treatment of psychiatric disorders such as depression, schizophrenia; anti-epileptics and anticonvulsants; Huntington's disease, aging and Alzheimer's disease; neuroprotective agents (such as excitatory amino acid antagonists and neurotropic factors) and neuroregenerative agents; trophic factors such as brain derived neurotrophic factor, ciliary neurotrophic factor, or nerve growth factor; drugs aimed at the treatment of CNS trauma or stroke; and drugs for the treatment of addiction and drug abuse; autacoids and anti-inflammatory drugs; chemotherapeutic agents for parasitic infections and microbial diseases; immunosuppressive agents and anti-cancer drugs; hormones and hormone antagonists; heavy metals and heavy metal antagonists; antagonists for non-metallic toxic agents; cytostatic agents for the treatment of cancer; radiation therapy immunoactive and immunoreactive agents; and a number of other agents such as transmitters and their respective receptor-agonists and -antagonists, their respective precursors or metabolites; antibiotics, antispasmodics, antihistamines, antinauseants, relaxants, stimulants, "sense" and "anti-sense" oligonucleotides, cerebral dilators, psychotropics, anti-manics, vascular dilators and constrictors, anti-hypertensives, migraine treatments, hypnotics, hyper- or hypo-glycemic agents, mineral or nutritional agents, anti-obesity drugs, anabolics and anti-asthmatics.

A number of suitable therapeutic agents are described in Gilman et al. (1990), "Goodman and Gilman's—The Pharmacological Basis of Therapeutics", Pergamon Press, New York, and include the following agents: acetylcholine and synthetic choline esters, naturally occurring cholinomimetic alkaloids and their synthetic congeners, anticholinesterase agents, ganglionic stimulants, atropine, scopolamine and related antimuscarinic drugs, catecholamines and sympathomimetic drugs, such as epinephrine, norepinephrine and dopamine, adrenergic agonists, adrenergic receptor antagonists, transmitters such as γ-amino butyric acid (GABA), glycine, glutamate, acetylcholine, dopamine, 5-hydroxytryptamine, and histamine, neuroactive peptides; analgesics and anesthetics such as opioid analgesics and antagonists; preanesthetic and anesthetic medications such as benzodiazepines, barbiturates, antihistamines, phenothiazines and butylphenones; opioids; antiemetics; anticholinergic drugs such as atropine, scopolamine or glycopyrrolate; cocaine; chloral derivatives; ethchlorvynol; glutethimide; methyprylon; meprobamate; paraldehyde; disulfiram; morphine, fentanyl and naloxone; centrally active antitussive agents; psychiatric drugs such as phenothiazines, thioxanthenes and other heterocyclic compounds (e.g., halperiodol); tricyclic antidepressants such as desimipramine and imipramine; atypical antidepressants (e.g., fluoxetine and trazodone), monoamine oxidase inhibitors such as isocarboxazid; lithium salts; anxiolytics such as chlordiazepoxyd and diazepam; anti-epileptics including hydantoins, anticonvulsant barbiturates, iminostilbines (such as carbamazepine), succinimides, valproic acid, oxazolidinediones and benzodiazepines; anti-Parkinson drugs such as L-DOPA/CARBIDOPA, D2 and D3 agonists and antagonists, apomorphine, amantadine, ergolines, selegeline, ropinorole, bromocriptine mesylate and anticholinergic agents; antispasticity agents such as baclofen, diazepam and dantrolene; neuroprotective agents, such as excitatory amino acid antagonists, neurotrophic factors and brain derived neurotrophic factor, ciliary neurotrophic factor, or nerve growth factor; neurotrophin (NT) 3 (NT3); NT4 and NT5; gangliosides; neuroregenerative agents; drugs for the treatment of addiction and drug abuse include opioid antagonists and anti-depressants; autocoids and anti-inflammatory drugs such as histamine, bradykinin, kallidin and their respective agonists and antagonists; chemotherapeutic agents for parasitic infections and microbial diseases; anti-cancer drugs including alkylating agents (e.g., nitrosoureas) and antimetabolites; nitrogen mustards, ethylenamines and methylmelamines; alkylsulfonates; folic acid analogs; pyrimidine analogs, purine analogs, vinca alkaloids; antibiotics; and drugs suitable for treating Alzheimer's Disease, where such drugs include memantine (1-amino-3,5-dimethyl-adamantane), donepezil HCl (2-[(1-benzyl-4-piperidyl)methyl]-5,6-dimethoxy-2,3-dihydroinden-1-one), rivastigmine (S)-N-Ethyl-N-methyl-3-[1-(dimethylamino)ethyl]-phenyl carbamate), galantamine ((4aS,6R,8aS)-5,6,9,10,11,12-hexahydro-3-methoxy-11-methyl-4aH-[1]benzofuro[3a,3,2-ef][2]benzazepin-6-ol), and tacrine (1,2,3,4-tetrahydroacridin-9-amine).

Cancer Chemotherapeutic Agents

In some embodiments, the at least a second functional moiety is a cancer chemotherapeutic agent. Cancer chemotherapeutic agents are non-peptidic (i.e., non-proteinaceous) compounds that reduce proliferation of cancer cells, and encompass cytotoxic agents and cytostatic agents. Cancer chemotherapeutic agents include antimetabolite agents, microtubule affecting agents, hormone modulators, metal complexes, taxanes, biological response modifiers, etc., as described below.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and progestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose), where PEG is poly(ethylene glycol).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Suitable biological response modifiers include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-alpha (IFN-α); (7) interferon-gamma (IFN-γ); (8) colony-stimulating factors; and (9) inhibitors of angiogenesis.

Additional Modifications

In some embodiments, the functionalized MNP further comprises an apolipoprotein (e.g., apoA, apoB, or apoE) attached to the functionalized MNP. The apolipoprotein provides for binding to endothelial cells of the BBB, and thus provides for transit of the functionalized MNP across the BBB.

In some embodiments, the functionalized MNP is further processed by attaching human serum albumin and/or apolipoprotein to the functionalized MNP. Human serum albumin (HSA) is attached, covalently or non-covalently (e.g., via ionic interactions) to the functionalized MNP via an acetyl group, via an amino group, via a poly(ethylene glycol) (PEG) linker, or via a thiol bond. Apolipoprotein, or a functional fragment thereof, is attached to the HSA, either covalently or non-covalently. See, e.g. Muller and Keck ((2004) *J. Nanosci. Nanotechnol.* 4:471); and Kreuter et al. ((2002) *J. Drug Target.* 10:317). Amino acid sequences of apolipoproteins are known in the art; for example, amino acid sequences of apoE polypeptides are found at e.g., GenBank Accession Nos. AAD02505; and AAB59397.

In other embodiments, the functionalized MNP further comprises apolipoprotein attached to the functionalized MNP via polysorbate-80. In some embodiments, the functionalized MNP is further processed by attaching polysorbate-80 covalently or non-covalently to the functionalized MNP. In some embodiments, the polysorbate-80 is attached via an acetyl group, via an amino group, via a PEG linker, or via a thiol bond directly to the coating layer. Apolipoprotein is attached to the polysorbate-80, either covalently or non-covalently.

Compositions

The present disclosure further provides compositions, including pharmaceutical compositions, comprising a subject functionalized magnetic nanoparticle. Compositions comprising a subject functionalized magnetic nanoparticle can include one or more of the following: a salt; a buffer; a pH adjusting agent; a non-ionic detergent; a protease inhibitor; a nuclease inhibitor; and the like.

A pharmaceutical composition comprising a subject 2DG-functionalized MNP will comprise one or more pharmaceutically acceptable carriers. As used herein, "pharmaceutically acceptable carrier" includes any material which, when combined with an active ingredient of a composition, allows the ingredient to retain biological activity and without causing disruptive reactions with the subject's immune system or other physiological function. Examples include, but are not limited to, any of the standard pharmaceutical carriers such as a phosphate buffered saline solution, water, glycerol, dextrose, emulsions such as oil/water emulsion, and various types of wetting agents. Exemplary diluents for aerosol or parenteral administration are phosphate-buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton, Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton, Pa. 18042, USA; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

In some embodiments, a subject 2DG-functionalized MNP is present in a liquid composition at a concentration of from about 1 mg particle weight per ml to about 25 mg particle weight per ml, e.g., from about 1 mg particle weight per ml to about 2 mg particle weight per ml, from about 2 mg particle weight per ml to about 5 mg particle weight per ml, from about 5 mg particle weight per ml to about 7 mg particle weight per ml, from about 7 mg particle weight per ml to about 10 mg particle weight per ml, from about 10 mg particle weight per ml to about 12 mg particle weight per ml, from about 12 mg particle weight per ml to about 15 mg particle weight per ml, from about 15 mg particle weight per ml to about 20 mg particle weight per ml, or from about 20 mg particle weight per ml to about 25 mg particle weight per ml.

A subject 2DG-functionalized magnetic nanoparticle can be formulated into preparations for injection, for inhalation (e.g., for nasal delivery, for delivery via the respiratory tract), for oral delivery (e.g., oral delivery to the gastrointestinal tract), for delivery through the gastrointestinal tract, for delivery via the genito-urinary tract, for ocular delivery, or for delivery via the skin (e.g., topical delivery via the skin).

In some embodiments, a subject 2DG-functionalized MNP is suspended in normal saline. In some embodiments, a subject 2DG-functionalized MNP is suspended in deionized water. In some embodiments, a subject 2DG-functionalized MNP is suspended in a liquid solution comprising dextrose.

Formulations Suitable for Injection

A subject 2DG-functionalized magnetic nanoparticle can be formulated into preparations for injection by dissolving, suspending, or emulsifying in an aqueous solvent, or a non-aqueous solvent, such as vegetable or other similar oils, synthetic aliphatic acid glycerides, esters of higher aliphatic acids or propylene glycol. In some embodiments, the formulation will include one or more conventional additives such as solubilizers, isotonic agents, suspending agents, emulsifying agents, stabilizers, and preservatives. Injectable formulations include, but are not limited to, formulations suitable for intravenous injection, formulations suitable for intramuscular injection, formulations suitable for intraocular injection, formulations suitable for peritumoral or intratumoral injection, and formulations for subcutaneous injection.

Formulations Suitable for Delivery Via the Gastrointestinal or Genito-Urinary Tract In some embodiments, a subject 2DG-MNP is formulated as a gel, as a solution, a solid, a semi-solid, or in some other form suitable for intravaginal administration. In a further exemplary embodiment, a subject 2DG-MNP is formulated as a gel, as a solution, a solid, a semi-solid, or in some other form suitable for rectal (e.g., intrarectal) administration.

A subject 2DG-MNP can be formulated for delivery via the genito-urinary tract by formulating the 2DG-MNP in a suppository. A subject 2DG-MNP can be made into suppositories by mixing with a variety of bases such as emulsifying bases or water-soluble bases. A subject 2DG-MNP can be administered rectally via a suppository. The suppository can include vehicles such as cocoa butter, carbowaxes and polyethylene glycols, which melt at body temperature, yet are solidified at room temperature. For suppositories, the composition can include traditional binders and carriers such as, polyalkylene glycols, or triglycerides. Such suppositories may be formed from mixtures containing the active ingredient in the range of about 0.5% to about 10% (w/w), e.g. about 1% to about 2%.

A subject 2DG-MNP will in some embodiments be formulated for vaginal delivery. A subject formulation for intravaginal administration can be formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject 2DG-MNP will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

Oral Formulations

In some embodiments, a subject 2DG-MNP is formulated for oral delivery. For oral preparations, a subject 2DG-MNP can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

For oral delivery, a subject formulation comprising a subject 2DG-MNP will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject 2DG-MNP is formulated with one or more pharmaceutical excipients and coated with an enteric coating, as described in U.S. Pat. No. 6,346,269. Suitable excipients include pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. The formulation can include a stabilizer, where suitable stabilizers include alkali-metals and alkaline earth metals, bases of phosphates and organic acid salts and organic amines. The formulation can also include one or more of talc, stearic acid, stearate, sodium stearyl fumarate, glyceryl behenate, kaolin and aerosil. The formulation can also include one or more of polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). The formulation can also include one or more of glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject 2DG-MNP formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B. V.).

Suitable oral formulations also include a subject 2DG-MNP formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

A formulation comprising a subject 2DG-MNP can also include an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Inhalational Formulations

A subject 2DG-MNP will in some embodiments be administered to a patient by means of a pharmaceutical delivery system for the inhalation route. A subject 2DG-MNP can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject 2DG-MNP to mucosal linings of the bronchi. This invention can utilize a system that depends on the power of a compressed gas to expel the 2DG-MNP from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains a subject 2DG-MNP, which can be suspended or emulsified in a mixture of a fluid carrier and a propellant. The aerosol can be in the form of a solution, suspension, emulsion, powder, or semi-solid preparation. Aerosols are intended for administration as fine, solid particles or as liquid mists via the respiratory tract of a patient. Various types of propellants known to one of skill in the art can be utilized. Suitable propellants include, but are not limited to, hydrocarbons such as dichlorodifluoromethane, propane, etc.; nitrogen; and the like. In the case of the pressurized aerosol, the dosage unit may be determined by providing a value to deliver a metered amount.

A subject 2DG-MNP can also be formulated for delivery with a nebulizer, which is an instrument that generates very fine liquid particles of substantially uniform size in a gas. For example, a liquid containing a subject 2DG-MNP is dispersed as droplets. The small droplets can be carried by a current of air through an outlet tube of the nebulizer. The resulting mist penetrates into the respiratory tract of the patient. A subject 2DG-MNP is in some embodiments formulated as a nasal spray.

A subject 2DG-MNP can be formulated in a powder composition, with or without a lubricant, carrier, or propellant. This embodiment can be used with a conventional device for administering a powder pharmaceutical composition by inhalation. For example, a powder mixture of the 2DG-MNP and a suitable powder base such as lactose or starch may be presented in unit dosage form in for example capsular or cartridges, e.g. gelatin, or blister packs, from which the powder may be administered with the aid of an inhaler, with or without a lubricant, carrier, or propellant. This embodiment can be carried out with a conventional device for administering a powder pharmaceutical composition by inhalation. For example, a powder mixture of the 2DG-MNP and a suitable powder base such as lactose or starch may be presented in unit dosage form in for example capsular or cartridges, e.g. gelatin, or blister packs, from which the powder may be administered with the aid of an inhaler.

A subject 2DG-MNP can be formulated with a low boiling point propellant. Such formulations are generally administered by conventional meter dose inhalers (MDI's). A subject 2DG-MNP can be formulated in an aqueous or ethanolic solution and delivered by a conventional nebulizer. A subject 2DG-MNP can be formulated into a dry powder formulation. Such a formulation can be administered by simply inhaling the dry powder formulation after creating an aerosol mist of the powder.

Formulations Suitable for Ocular Delivery

A subject 2DG-MNP will in some embodiments be formulated for ocular delivery, e.g., where a subject 2DG-MNP is formulated for delivery to the eye in liquid form (e.g., eye drops), for injection into or around the eye, etc.

A subject 2DG-MNP can be formulated in an ophthalmic pharmaceutical composition. Ophthalmic pharmaceutical compositions can be adapted for topical administration to the eye in the form of solutions, suspensions, ointments, creams or as a solid insert.

For ocular formulations, a subject 2DG-MNP can be conveniently admixed with a non-toxic pharmaceutical organic carrier, or with a non-toxic pharmaceutical inorganic carrier. Suitable pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation can also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The ocular formulation can also be in the form of a microparticle formulation. The ocular formulation can also be in the form of a solid insert. For example, one may use a solid water soluble polymer as the carrier for the medicament. The polymer used to form the insert can be any water soluble non-toxic polymer, for example, cellulose derivatives such as methylcellulose, sodium carboxymethyl cellulose, (hydroxyl-lower alkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

A formulation comprising a subject 2DG-MNP can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

Topical Formulations

A subject 2DG-MNP can be formulated for topical administration to the skin. For example, a subject 2DG-MNP can be formulated with one or more dermatologically acceptable excipients.

The term "dermatologically acceptable," as used herein, means that the compositions or components thereof so described are suitable for use in contact with mammalian skin (e.g., human skin) without undue toxicity, incompatibility, instability, allergic response, and the like.

In some embodiments, a subject 2DG-MNP is formulated with a dermatologically active acid. Suitable dermatologically active acids include a hydroxy acid, ascorbic acid, glycolic acid, magnesium ascorbyl phosphate, sodium ascorbyl phosphate, sodium ascorbate, ascorbyl glucosides, salicylic acid, lipoic acid, dihydrolipoic acid, and combinations thereof. In some embodiments, the dermatologically active acid is alpha-hydroxy acid. Alpha-hydroxy acids include, malic acid, tartaric acid, lactic acid, pyruvic acid, citric acid, and combination of any of the foregoing. In some embodiments, a subject 2DG-MNP is formulated with a dermatologically active acid and one or more of: ammonium hydroxide, alkali hydroxide, alkanolamone, amino acid, sodium hydroxide, potassium hydroxide, diethanolamine, triethanolamine, 2-dimethylaminoethanol (dimethyl MEA), aminobutanol, arginine, and lysine.

Suitable excipients include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

A variety of emollients can be used. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; wax esters such as beeswax, spermaceti, myristyl myristate, stearyl stearate; forming a mixture of ether esters; and vegetable waxes including, but not limited to, carnauba and candelilla waxes; and cholesterol fatty acid esters.

Humectants of the polyhydric alcohol-type are suitable for use. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof.

Also suitable for inclusion in a formulation for topical application (e.g., to the skin) are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

A composition comprising a subject 2DG-MNP can include a dermatologically-acceptable hydrophilic diluent. Non-limiting examples of hydrophilic diluents are water, organic hydrophilic diluents such as lower monovalent alcohols (e.g., $C_1$-$C_4$ alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. A composition comprising a subject 2DG-MNP can contain from about 60% to about 99.99% of a hydrophilic diluent.

A composition comprising a subject 2DG-MNP can include a dermatologically acceptable carrier. An example of a suitable carrier is an emulsion comprising a hydrophilic phase comprising a hydrophilic component, e.g., water or other hydrophilic diluent, and a hydrophobic phase comprising a hydrophobic component, e.g., a lipid, oil or oily material. The hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions can comprise from about 1% to about 50% of the dispersed hydrophobic phase and from about 1% to about 98% of the continuous hydrophilic phase; water-in-oil emulsions can comprise from about 1% to about 98% of the dispersed hydrophilic phase and from about 1% to about 50% of the continuous hydrophobic phase.

A subject 2DG-MNP can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The topical formulation can include thickening agents such as cellulose and/or cellulose derivatives. The topical formulation can include contain gums such as xanthan, guar or carbo gum or gum arabic, or alternatively poly(ethylene glycol)s, bentones and montmorillonites, and the like.

Utility

The present disclosure further provides various applications in which a subject functionalized magnetic nanoparticle finds utility, including research applications, diagnostic applications, and treatment applications.

Research Applications

The present disclosure provides research applications using a subject 2DG-functionalized MNP. A subject functionalized magnetic nanoparticle is injected into a subject (e.g., a non-human animal such as a non-human primate, a rodent, etc.), and the 2DG-functionalized MNP is detected by imaging. Research applications include assaying the effect of a given test agent on a particular disease. Research applications further include testing the effect of various external and internal stimuli on normal and diseased brain tissue. Research applications further include testing the effect of a test agent on a cancerous tissue, and all other applications that require administration of 2DG or compounds that contain 2DG.

Diagnostic Methods

The present disclosure provides diagnostic methods for identifying or detecting a specific tissue. The methods generally involve administering to an individual a subject 2DG-functionalized MNP; and imaging a tissue to which the 2DG-functionalized MNP is bound. For example, a liquid pharmaceutical composition comprising a subject 2DG-functionalized MNP is administered to the individual (e.g., by intravenous injection); and the 2DG-functionalized MNP is detected by an imaging technique. A subject method permits imaging of a particular tissue in a living subject. A subject method permits detection of diseased tissue, and also provide a way for physicians to monitor the progress of patients undergoing treatment for the disease. In some embodiments, the imaging is by magnetic resonance imaging (MRI). In some embodiments, the imaging is by positron emission tomography (PET). In some embodiments, the imaging is by computed tomography (CT).

Tissues that can be detected using a subject 2DG-functionalized MNP include, but are not limited to, tissues affected by one or more of the following diseases, disorders, and conditions: a neoplasm; Alzheimer's Disease; Huntington's Disease; Parkinson's Disease; amyotrophic lateral sclerosis, cardiac diseases; acute and chronic inflammatory diseases such as lupus and sarcoidosis; infectious diseases; vascular diseases; gastro-intestinal diseases; diseases of bone and bone marrow; congenital diseases; diabetes; obesity; kidney diseases; muscular diseases; diseases of fatty tissues; psychological, cognitive, and psychiatric disorders such as autism, depression, addiction, and schizophrenia; diseases of the pancreas; diseases of the urinary tract; diseases of reproductive organs; genetic diseases; diseases of, or associated with, impaired metabolic activity; diseases and disorders of the central nervous system; diseases of the lymphatic system; and pathologic, pathologic, or non-pathologic systemic and central changes associated with acute or chronic use of medications, medicinal substances, or illicit substances. A subject 2DG-functionalized MNP can also be used for tracking of and/or detecting viability of transplant tissues, stem cells, and the like.

A composition comprising a subject 2DG-functionalized MNP can be administered to an individual via a parenteral route of administration, e.g., intravenous, intramuscular, subcutaneous, intratumoral, intracranial, peritumoral, inhalational (e.g., nasal; via the respiratory tract), ocular, topically to the skin, via the genito-urinary tract, etc. A composition comprising a subject 2DG-MNP can be administered to an individual via an enteral route of administration, e.g., via an oral route of administration, via a gastrointestinal route of administration, or via rectal administration.

A suitable number of 2DG-functionalized MNP are administered to an individual, where a suitable number ranges from about $10^2$ 2DG-functionalized MNP to about $10^{18}$ 2DG-functionalized MNP, e.g., from about $10^2$ to about $10^3$ 2DG-functionalized MNP, from about $10^3$ to about $10^4$ 2DG-functionalized MNP, from about $10^4$ to about $10^5$ 2DG-functionalized MNP, from about $10^5$ to about $10^6$ 2DG-functionalized MNP, from about $10^6$ to about $10^7$ 2DG-functionalized MNP, from about $10^7$ to about $10^8$ 2DG-functionalized MNP, from about $10^8$ to about $10^9$ 2DG-functionalized MNP, from about $10^9$ 2DG-functionalized MNP to about $10^{10}$ 2DG-functionalized MNP, from about $10^{10}$ 2DG-functionalized MNP to about $10^{12}$ 2DG-functionalized MNP, from about $10^{12}$ 2DG-functionalized MNP to about $10^{14}$ 2DG-functionalized MNP, from about $10^{14}$ 2DG-functionalized MNP to about $10^{16}$ 2DG-functionalized MNP, or from about $10^{16}$ 2DG-functionalized MNP to about $10^{18}$ 2DG-functionalized MNP.

In some embodiments, the outcome of a subject diagnostic method is provided in a report. Thus, in some embodiments, a subject method further includes a step of preparing or generating a report that includes information regarding the results of the imaging method (e.g., detecting step). For example, a subject method can further include a step of generating or outputting a report providing the results of the imaging method (e.g., whether an individual has a tumor, size of the tumor, location of the tumor) etc.; whether an individual has an epileptic lesion, the size of the lesion, the location of the lesion, etc.), which report can be provided in the form of an electronic medium (e.g., an electronic display on a computer monitor), or in the form of a tangible medium (e.g., a report printed on paper or other tangible medium).

Detection of Brain Activity and/or Function

In some embodiments, a subject diagnostic method provides for detection of brain activity and function. Administration of a subject 2DG-functionalized MNP to an individual (e.g., a living individual) allows detection of brain activity and/or function. Following administration of a subject 2DG-functionalized MNP to an individual, brain activity in a particular area or areas of the brain can be detected. Areas of the brain in which a subject method can be used to detect activity and/or function include, but are not limited to, e.g., neocortex, entorhinal cortex, somatosensory cortex, thalamus, hypothalamus, hippocampus, amygdala, olfactory bulb, motor cortex, frontal lobe, parietal lobe, occipital lobe, temporal lobe, cerebellum, brain stem, medulla, pons, basal ganglia, globus pallidum, striatum, etc. Brain activity can be detected in response to an internal or external stimulus, or in connection with a disease state or disease event.

Exemplary external stimuli include visual stimuli, odors, auditory stimuli (e.g., sounds), electrical stimulation (e.g., applied to the skin), touch stimuli, taste stimuli, etc. For example, an external stimulus is applied for a period of time (e.g., less than one second, from about 1 second to about 1 minute, from about 1 minute to about 30 minutes, from about 30 minutes to about 1 hour, or more than 1 hour); a subject 2DG-MNP is administered before, during, or after the external stimulus has been applied; and the effect, if any, of the external stimulus on brain activity is detected by detecting the 2DG-MNP in the brain.

Exemplary internal stimuli include, e.g., ingested substances, topically applied substances, administered substances (e.g., administered to a subject via any route of administration, including, but not limited to, oral, topically to the skin, intravenous, intramuscular, via inhalation, etc.), and inhaled substances, where such substances include, but are not limited to, psychoactive compounds, anti-depressants, stimulants, anti-seizure agents, anti-hallucinogenic agents, etc. For example, a substance is administered to a subject; a subject 2DG-MNP is administered before, during, or after the substance has been administered; and the effect, if any, of the substance is detected by detecting the 2DG-MNP in the brain.

Exemplary disease states include, but are not limited to, epilepsy, a neurodegenerative disease, etc. Exemplary disease events include, but are not limited to, an epileptic seizure, a hallucination, and the like. For example, preceding a disease state or event, during a disease state or event, or following a disease state or event, a subject 2DG-MNP is administered before, during, or after the substance has been administered; and the effect, if any, of the disease state or disease event on brain function and/or activity is detected by detecting the 2DG-MNP in the brain.

Tumor Detection

In some embodiments, a subject method provides for detection of a tumor, wherein a subject 2DG-functionalized MNP exhibits differential affinity for the tumor, compared to the affinity of the 2DG-functionalized MNP for a normal (non-cancerous) tissue. In some embodiments, a subject method provides for detection of a tumor, wherein a subject 2DG-functionalized MNP exhibits differential metabolic uptake by the tumor, compared with the metabolic uptake of the 2DG-functionalized MNP for normal (non-cancerous) tissue.

In some embodiments, a subject 2DG-functionalized MNP provides for detection of a tumor that has a size (e.g., average diameter) of less than about 5 cm, less than about 2 cm, less than about 1.5 cm, less than about 1 cm, less than about 0.5 cm, less than about 250 mm, less than about 100 mm, less than about 50 mm, less than about 10 mm, less than about 1 mm, or less than about 0.5 mm. For example, a subject 2DG-functionalized MNP provides for detection of a tumor that has a size (e.g., average diameter) of from about 0.5 mm to about 1 mm to about 5 mm, from about 5 mm to about 10 mm, from about 10 mm to about 25 mm, from about 25 mm to about 50 mm, from about 50 mm to about 100 mm, from about 100 mm to about 250 mm, from about 250 mm to about 500 mm, from about 500 mm to about 750 mm, from about 750 mm to about 1.0 cm, from about 1.0 cm to about 1.5 cm, from about 1.5 cm to about 2 cm, from about 2 cm to about 2.5 cm, from about 2.5 cm to about 3 cm, from about 3 cm to about 4 cm, or from about 4 cm to about 5 cm, or greater than 5 cm.

For tumor detection, a subject 2DG-functionalized MNP can be administered parenterally, e.g., intravenously, via inhalation, via ocular administration, via topical administration to the skin, or via another parenteral route of administration. For tumor detection, a subject 2DG-functionalized MNP can be administered via an enteral route of administration, e.g., via an oral route of administration, via a gastrointestinal route of administration, or via rectal administration.

A subject method is useful for detecting a wide variety of neoplasms, including carcinomas, sarcomas, leukemias, and lymphomas. In some embodiments, the tumor is a solid tumor.

Carcinomas that can be detected using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be detected using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be detected using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be detected using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be detected using a subject method include, but are not limited to, B-cell lymphomas (e.g., Burkitt's lymphoma); Hodgkin's lymphoma; and the like.

In some embodiments, the outcome of a subject diagnostic (detection) method is provided in a report. Thus, in some embodiments, a subject method further includes a step of preparing or generating a report that includes information regarding the results of the imaging method (e.g., detecting step). For example, a subject method can further include a step of generating or outputting a report providing the results of the imaging method (e.g., whether an individual has a tumor, size and/or shape of the tumor, location of the tumor, or other characteristics of the tumor), which report can be provided in the form of an electronic medium (e.g., an electronic display on a computer monitor), or in the form of a tangible medium (e.g., a report printed on paper or other tangible medium).

Detection of Epileptic Tissue

In some embodiments, a subject method provides for detection of epileptic tissue, e.g., a tissue affected by an epileptic seizure. The methods generally involve administering a composition comprising a subject 2DG-functionalized MNP to an individual; and detecting binding of the 2DG-functionalized MNP to a brain tissue in the individual. Administration of the 2DG-functionalized MNP to the individual can be carried out before, during, or after an epileptic seizure. For example, in some embodiments, a composition comprising a 2DG-functionalized MNP is administered to an individual from about 1 minute to about 5 minutes, from about 5 minutes to about 10 minutes, from about 10 minutes to about 15 minutes, from about 15 minutes to about 30 minutes, from about 30 minutes to about 60 minutes, from about 1 hour to about 2 hours, from about 2 hours to about 4 hours, from about 4 hours to about 8 hours, or more than 8 hours, following an epileptic seizure. In some embodiments, a composition comprising a subject 2DG-functionalized MNP is administered interictally.

In some embodiments, the outcome of a subject diagnostic method is provided in a report. Thus, in some embodiments, a subject method further includes a step of preparing or generating a report that includes information regarding the results of the imaging method (e.g., detecting step). For example, a subject method can further include a step of generating or outputting a report providing the results of the imaging method (e.g., whether an individual has an epileptic lesion, the size of the lesion, the location of the lesion, etc.), which report can be provided in the form of an electronic medium (e.g., an electronic display on a computer monitor), or in the form of a tangible medium (e.g., a report printed on paper or other tangible medium).

Predictive Methods

A subject 2DG-functionalized MNP (2DG-MNP) can also be used as surrogate markers in methods of predicting (determining the likelihood) that an individual will develop a particular disease. Thus, the present disclosure provides methods of determining the likelihood that an individual will develop a disease, the methods generally involving: a) administering to the individual a 2DG-MNP; and b) detecting binding of the 2DG-MNP to a tissue in the individual; where the results of the detection step can provide for a prediction that the individual has a higher likelihood of developing a particular disease than a reference control, or can provide for a prediction that the individual will likely not develop the disease. In some embodiments, the methods further comprise generating a report that includes the prediction. In some embodiments, the report further includes a treatment recommendation for the individual. In some embodiments, a subject predictive method (disease likelihood assessment method) further comprises treating the individual.

For example, where the level of binding of a subject 2DG-MNP to a particular tissue is at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a subject 2DG-MNP to a tissue that is known not to be diseased), a prediction can be made that the individual has a likelihood of developing a disease associated with that particular tissue, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop the disease.

For example, where the level of binding of a subject 2DG-MNP to (or metabolic uptake into) a breast tissue in a female individual (e.g., a female human) is at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a subject 2DG-MNP to a breast tissue that is known not to be diseased; the level of metabolic uptake of a subject 2DG-MNP into a breast tissue that is known not to be diseased), a prediction can be made that the individual has a likelihood of developing breast cancer, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop breast cancer.

For example, where the level of binding of a subject 2DG-MNP to a prostate tissue in a male individual (e.g., a male human) is at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a subject 2DG-MNP to a prostate tissue that is known not to be diseased), a prediction can be made that the individual has a likelihood of developing prostate cancer, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop prostate cancer.

As another example, where the level of binding of a subject 2DG-MNP to a brain tissue in an individual who has undergone traumatic head injury is at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a subject 2DG-MNP to a brain tissue that is known not to be diseased), a prediction can be made that the individual has a likelihood of having at least one epileptic event (e.g., an epileptic seizure), where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will have such an epileptic event.

As noted above, in some embodiments, a subject predictive method will further comprise generating a report. For example, a subject method can further include a step of generating or outputting a report providing the results of a subject likelihood assessment, which report can be provided in the form of an electronic medium (e.g., an electronic display on a computer monitor), or in the form of a tangible medium (e.g., a report printed on paper or other tangible medium). The report will include at least the prediction (likelihood assessment), and can include further information such as: a) the results of the detection step; b) personal information about the individual such as age, weight, gender, etc.; c) medical information about the individual, e.g., family history of the disease, prior treatment for a disease, genetic information (e.g., genotyping results relating to the disease), and the like.

The report can further include a treatment recommendation(s). Where the results indicate a likelihood of disease development, the recommendation can include a recommendation that a treatment regimen is indicated. Where the results indicate that development of disease is not likely, the recommendation can include a recommendation for no treatment, or can include a recommendation for further evaluation of the patient. For example, where an individual who has undergone traumatic head injury is assessed using a subject method, and the results indicate that the individual is likely to experience at least one epileptic seizure, prophylactic administration of an anti-seizure agent can be recommended. As another example, where the individual being tested is a human female, and the results of a subject predictive method indicate that the individual will likely develop breast cancer, the recommendation can include: a) a recommendation that the individual be further evaluated for breast cancer; and/or b) a recommendation that the individual be treated with an anti-cancer agent suitable for treating early stage breast cancer.

Computer-Readable Storage Medium

The present disclosure also contemplates a computer-readable storage medium (e.g. compact disc-read only memory (CD-ROM), memory key, flash memory card, diskette, etc.) having stored thereon a program which, when executed in a computing environment, provides for implementation of a disease likelihood assessment as described above. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

The present disclosure further provides a computer-based system that includes a processor-readable medium comprising code representing instructions to generate a prediction of likelihood that an individual will develop a disease, based on data generated by the detection step of a subject predictive method. A subject computer-based system involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., results of an imaging method used to detect 2DG-MNP binding to, and/or metabolic uptake into, a tissue in a living individual, as described above); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include electronic mail, interactive television, and the like. In an embodiment of particular interest, all or a portion of the input data and/or all or a portion of the output data (e.g., usually at least the final report) are maintained on a web server for access, e.g., confidential access, with typical browsers. The data may be accessed or sent to health professionals as desired. The input and output data, including all or a portion of the final report, can be used to populate a patient's medical record which may exist in a confidential database at the healthcare facility.

Treatment Applications

The present disclosure provides methods of treating a disease, disorder, or condition, the methods generally involving administering to an individual in need thereof an effective amount of a subject 2DG-functionalized MNP. In some embodiments, a subject treatment method involves administering to an individual in need thereof an effective amount of a subject 2DG-functionalized MNP, where the 2DG-functionalized MNP further comprises at least a second functional moiety, where the at least a second functional moiety is a therapeutic agent that is effective to treat the disease, disorder, or condition. In some embodiments, a subject treatment method involves: a) administering to an individual in need thereof a composition comprising a subject 2DG-functionalized MNP, where the 2DG-functionalized MNP provides for detection of a diseased tissue; and b) subjecting the individual to a treatment regimen for the disease detected by the 2DG-functionalized MNP.

A composition comprising a subject 2DG-functionalized MNP can be administered to an individual via a parenteral route of administration, e.g., intravenous, intramuscular, subcutaneous, intratumoral, intracranial, peritumoral, inhalational, ocular, topical (e.g., to the skin), via the genito-urinary tract, etc. A composition comprising a subject 2DG-MNP can be administered to an individual via an enteral route of administration, e.g., via an oral route of administration, via a gastrointestinal route of administration, or via rectal administration.

In some embodiments, a pharmaceutical composition comprising a subject 2DG-functionalized MNP is administered to an individual in need thereof, where the subject 2DG-functionalized MNP comprises a therapeutic agent. In some embodiments, a subject pharmaceutical composition comprising a subject 2DG-functionalized MNP is administered to an individual in need thereof, where the subject 2DG-functionalized MNP comprises a therapeutic agent, where the route of administration is parenteral, e.g., intravenous, intramuscular, subcutaneous, intratumoral, intracranial, peritumoral, via inhalation, ocular, topical (e.g., to the skin), etc., or enteral, e.g., oral, rectal, via the gastrointestinal tract, etc.

An effective amount of a subject 2DG-functionalized MNP is an amount that is sufficient to at least ameliorate the symptoms of a disease, disorder, or condition. In some embodiments, an effective amount of a subject 2DG-functionalized MNP is an amount that is effective to reduce the severity and/or incidence of at least one symptom of a disease or disorder by at least about 10%, at least about 20%, at least about 25%, at least about 30%, at least about 40%, at least about 50%, at least about 60%, at least about 70%, at least about 80%, at least about 90%, or more, compared to the severity and/or incidence of the symptom in an individual not treated with the 2DG-functionalized MNP.

For example, an effective amount of a subject 2DG-functionalized MNP comprising a therapeutic agent is an amount that is sufficient to at least ameliorate the symptoms of a disease, disorder, or condition. In some embodiments, an effective amount of a subject 2DG-functionalized MNP comprising a therapeutic agent is an amount that is effective to reduce the severity and/or incidence of at least one symptom of a disease or disorder by at least about 10%, at least about 20%, at least about 25%, at least about 30%, at least about 40%, at least about 50%, at least about 60%, at least about 70%, at least about 80%, at least about 90%, or more, compared to the severity and/or incidence of the symptom in an individual not treated with the 2DG-functionalized MNP.

An effective amount of a subject 2DG-functionalized MNP will vary, depending on various factors including, e.g., the nature of the disease, disorder, or condition; the severity or extent of the disease, disorder, or condition; the age or other physical characteristics of the individual; and the like. Effective amounts include, e.g., from about $10^2$ to about $10^{18}$ 2DG-functionalized MNP, e.g., from about $10^2$ to about $10^3$ 2DG-functionalized MNP, from about $10^3$ to about $10^4$ 2DG-functionalized MNP, from about $10^4$ to about $10^5$ 2DG-functionalized MNP, from about $10^5$ to about $10^6$ 2DG-functionalized MNP, from about $10^6$ to about $10^7$ 2DG-functionalized MNP, from about $10^7$ to about $10^8$ 2DG-functionalized MNP, from about $10^8$ to about $10^9$ 2DG-functionalized MNP, from about $10^9$ 2DG-functionalized MNP to about $10^{10}$ 2DG-functionalized MNP, from about $10^{10}$ 2DG-functionalized MNP to about $10^{12}$ 2DG-functionalized MNP, from about $10^{12}$ 2DG-functionalized MNP to about $10^{14}$ 2DG-functionalized MNP, from about $10^{14}$ 2DG-functionalized MNP to about $10^{16}$ 2DG-functionalized MNP, or from about $10^{16}$ 2DG-functionalized MNP to about $10^{18}$ 2DG-functionalized MNP. As noted above, in some embodiments, the 2DG-functionalized MNP comprises a therapeutic agent.

Unit doses of 2DG-functionalized MNP can comprise from about from about $10^2$ to about $10^{18}$ 2DG-2DG-functionalized MNP, e.g., from about $10^2$ to about $10^3$ 2DG-functionalized MNP, from about $10^3$ to about $10^4$ 2DG-functionalized MNP, from about $10^4$ to about $10^5$ 2DG-functionalized MNP, from about $10^5$ to about $10^6$ 2DG-functionalized MNP, from about $10^6$ to about $10^7$ 2DG-functionalized MNP, from about $10^7$ to about $10^8$ 2DG-functionalized MNP, from about $10^8$ to about $10^9$ 2DG-functionalized MNP, from about $10^9$ 2DG-functionalized MNP to about $10^{10}$ 2DG-functionalized MNP, from about $10^{10}$ 2DG-functionalized MNP to about $10^{12}$ 2DG-functionalized MNP, from about $10^{12}$ 2DG-functionalized MNP to about $10^{14}$ 2DG-functionalized MNP, from about $10^{14}$ 2DG-functionalized MNP to about $10^{16}$ 2DG-functionalized MNP, or from about $10^{16}$ 2DG-functionalized MNP to about $10^{18}$ 2DG-functionalized MNP.

In some embodiments, a unit dose of a subject 2DG-functionalized MNP is expressed on the basis of the weight of the patient. For example, in some embodiments, a unit dose of a subject 2DG-functionalized MNP is from about 0.5 mg/kg to about 50 mg/kg, e.g., from about 0.5 mg/kg to about 1 mg/kg, from about 1 mg/kg to about 2.5 mg/kg, from about 2.5 mg/kg to about 5 mg/kg, from about 5 mg/kg to about 10 mg/kg, from about 10 mg/kg to about 15 mg/kg, from about 15 mg/kg to about 20 mg/kg, from about 20 mg/kg to about 25 mg/kg, from about 25 mg/kg to about 30 mg/kg, from about 30 mg/kg to about 35 mg/kg, from about 35 mg/kg to about 40 mg/kg, from about 40 mg/kg to about 45 mg/kg, or from about 45 mg/kg to about 50 mg/kg.

In some embodiments, multiple doses of a 2DG-functionalized MNP will be administered. For example, a unit dose of a 2DG-functionalized MNP will be administered is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

In some embodiments, a 2DG-functionalized MNP (e.g., a 2DG-functionalized MNP comprising a therapeutic agent) is administered at any suitable frequency, and over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Individuals in need of treatment include individuals having any of a variety of disorders, including, but not limited to, a neoplasm; Alzheimer's Disease; Huntington's Disease; Parkinson's Disease; amyotrophic lateral sclerosis, cardiac diseases; acute and chronic inflammatory diseases such as lupus and sarcoidosis; infectious diseases; vascular diseases; gastro-intestinal diseases; diseases of bone and bone marrow; congenital diseases; diabetes; obesity; kidney diseases; muscular diseases; diseases of fatty tissues; psychological, cognitive, and psychiatric disorders such as autism, depression, addiction, and schizophrenia; diseases of the pancreas; diseases of the urinary tract; diseases of reproductive organs; genetic diseases; diseases of, or associated with, impaired metabolic activity; diseases and disorders of the central nervous system; diseases of the lymphatic system; and pathologic, pathologic, or non-pathologic systemic and central changes associated with acute or chronic use of medications, medicinal substances, or illicit substances.

In some embodiments, a subject method provides for treatment of a neoplasm. In some embodiments, a subject treatment method involves administering to an individual having a neoplasm an effective amount of a subject 2DG-functionalized MNP, where the 2DG-functionalized MNP further comprises at least a second functional moiety, where the at least a second functional moiety is a cancer chemotherapeutic agent. Suitable cancer chemotherapeutic agents are listed above. In some embodiments, a cancer chemotherapeutic agent is linked to the 2DG moiety. In other embodiments, a cancer chemotherapeutic agent is linked to the biocompatible substrate.

In some embodiments, an effective amount of a 2DG-functionalized MNP comprising a cancer chemotherapeutic agent is an amount that, when administered in one or more doses, is effective to reduce tumor mass by at least about 5%, by at least about 10%, by at least about 15%, by at least about 20%, by at least about 25%, by at least about 50%, by at least about 75%, by at least about 80%, by at least about 90%, compared to the tumor mass in the absence of treatment with the 2DG-functionalized MNP comprising a cancer chemotherapeutic agent. In some embodiments, an effective amount of a 2DG-functionalized MNP comprising a cancer chemotherapeutic agent is an amount that, when administered in one or more doses, is effective to completely eradicate the tumor.

In some embodiments, a subject treatment method involves: a) administering to an individual in need thereof a composition comprising a subject 2DG-functionalized MNP, where the 2DG-functionalized MNP provides for detection of a diseased tissue; and b) subjecting the individual to a treatment regimen for the disease detected by the 2DG-functionalized MNP.

In some embodiments, a subject treatment method involves: a) administering to an individual having a tumor a composition comprising a subject 2DG-functionalized MNP, where the 2DG-functionalized MNP provides for detection of the tumor; and b) subjecting the individual to a treatment regimen for the tumor detected by the 2DG-functionalized MNP. Standard cancer therapies include surgery (e.g., surgical removal of cancerous tissue), radiation therapy, laser ablation, hyperthermia therapy, bone marrow transplantation, chemotherapeutic treatment, biological response modifier treatment, and certain combinations of the foregoing. Radiation therapy includes, but is not limited to, x-rays or gamma rays that are delivered from either an externally applied source such as a beam, or by implantation of small radioactive sources. For example, in some embodiments, in some embodiments, a subject treatment method involves: a) administering to an individual having a tumor a composition comprising a subject 2DG-functionalized MNP, where the 2DG-functionalized MNP is selectively taken up by the tumor and provides for detection of the tumor; b) detecting the tumor using a suitable imaging method (e.g., MRI, CT, etc.); and c) subjecting the individual to hyperthermia therapy to reduce the size and/or area and/or viability of the tumor. As another example, in some embodiments, in some embodiments, a subject treatment method involves: a) administering to an individual having a tumor a composition comprising a subject 2DG-functionalized MNP, where the 2DG-functionalized MNP is selectively taken up by the tumor and provides for detection of the tumor; b) detecting the tumor using a suitable imaging method (e.g., MRI, CT, etc.); and c) administering one or more cancer chemotherapeutic agents to the individual. As another example, in some embodiments, in some embodiments, a subject treatment method involves: a) administering to an individual having a tumor a composition comprising a subject 2DG-functionalized MNP, where the 2DG-functionalized MNP is selectively taken up by the tumor and provides for detection of the tumor; b) detecting the tumor using a suitable imaging method (e.g., MRI, CT, etc.); and c) subjecting the individual to radiation treatment for the cancer.

Disease Grading Methods

The present disclosure provides methods of grading a disease, disorder, or condition, the methods generally involving administering to an individual having, at risk of having, or suspected of having, a disease, disorder, or condition, a subject 2DG-functionalized MNP. Binding of the 2DG-functionalized MNP to a tissue or tissues in the body is detected, where the detection provides for grading of the disease. For example, the strength of the signal obtained from detection of tissue-bound 2DG-functionalize MNP is correlated with disease state. In some embodiments, a subject method provides for staging and/or grading a tumor.

In some embodiments, the disease stage is provided in a report. Thus, in some embodiments, a subject method further includes a step of preparing or generating a report that includes information regarding the disease stage. For example, a subject method can further include a step of generating or outputting a report providing the results of a subject disease grading method, which report can be provided in the form of an electronic medium (e.g., an electronic display on a computer monitor), or in the form of a tangible medium (e.g., a report printed on paper or other tangible medium).

Disease Monitoring Applications

The present disclosure provides methods of monitoring the progress of a disease, disorder, or condition, the methods generally involving administering to an individual having a disease a composition comprising a subject 2DG-functionalized MNP, and detecting binding of the 2DG-functionalized MNP to a tissue or tissues in the individual. A composition comprising a subject 2DG-functionalized MNP is administered at various times throughout the course of the disease, to monitor the state of the disease in the individual.

For example, in some embodiments, a subject method comprises: a) administering 2DG-functionalized MNPs at a first time to an individual having a disease, where a first image is produced; b) administering to the individual a subject 2DG-functionalized MNP at a second time to the individual, where the second time is from about 1 day to about 1 year after the first time (e.g., where the second time is from about 1 day to about 2 days, from about 2 days to about 1 week, from about 1 week to about 2 weeks, from about 2 weeks to about 1 month, from about 1 month to about 2 months, from about 2 months to about 4 months, from about 4 months to about 6 months, from about 6 months to about 8 months, or from about 8 months to about 1 year, after the first time); and c) comparing the first and second images produced following the first and the second administrations. Further administrations at further time points are also contemplated. In some embodiments the second image, compared to the first image, will indicate that the disease is progressing. In some embodiments the second image, compared to the first image, will indicate that the disease is regressing.

In some embodiments, the disease progress is provided in a report. Thus, in some embodiments, a subject method further includes a step of preparing or generating a report that includes information regarding the disease progression (e.g., tumor size, metastasis, etc.). For example, a subject method can further include a step of generating or outputting a report providing the results of a subject disease monitoring method, which report can be provided in the form of an electronic medium (e.g., an electronic display on a computer monitor), or in the form of a tangible medium (e.g., a report printed on paper or other tangible medium).

Determining Efficacy of Treatment

The present disclosure provides methods of determining efficacy of treatment with a given therapeutic agent, surgical procedure, radiation treatment, or other treatment regimen, the methods generally involving administering to an individual who has undergone a treatment regimen a composition comprising a subject 2DG-functionalized MNP, and detecting binding of the 2DG-functionalized MNP to a tissue or tissues in the individual. A subject 2DG-functionalized MNP binds to a diseased tissue, and provides for detection of the diseased tissue, where detection methods are as described above. Detection of a diseased tissue provides an indication of whether a treatment with a particular treatment regimen is effective.

In some embodiments, a subject method involves: a) administering to an individual who has undergone a first treatment regimen for a disease, disorder, or condition a composition comprising a subject 2DG-functionalized MNP; b) imaging a tissue or tissues in the individual to which the 2DG-functionalized MNP is bound; and c) recommending a treatment. The imaging step (b) provides an indication as to whether the first treatment regimen is efficacious in treating the disease, disorder, or condition. The imaging data are analyzed to determine whether the first treatment regimen was efficacious. For example, depending on whether the first treatment regimen is determined to be efficacious, a treatment regimen is recommended, which is the same or different from the first treatment regimen. If the first treatment regimen is deemed to be efficacious, it may be recommended to continue with the first treatment regimen (e.g., repeat the first treatment regimen), to carry out a second treatment regimen wherein an agent that is administered as part of the first treatment regimen is administered at a lower dose than in the first treatment regimen, or to discontinue treatment altogether. If the first treatment regimen is determined not to be efficacious, it may be recommended to carry out a second treatment regimen that is different from the first treatment regimen, e.g., it may be recommended to administer a different therapeutic agent than the therapeutic agent administered as part of the first treatment regimen.

For example, in some embodiments, an individual has undergone a treatment regimen for cancer, e.g., radiation treatment, surgical removal of cancerous tissue, chemotherapeutic treatment, or a combination of two or more such treatments. Efficacy of the treatment is determined by detecting cancerous tissue, if any, in the individual, in the days, weeks, months, or years following the treatment for the cancer. Cancerous tissue is detected, as described above, by administering to the individual a composition comprising a subject 2DG-functionalized MNP; and detecting binding of the 2DG-functionalized MNP to tissues in the individual. Depending on the analysis of the efficacy of the treatment regimen, a recommendation is made for: a) discontinuation of treatment; b) an alteration of the treatment regimen, e.g., to increase the dose and/or frequency of treatment; or c) a treatment regimen that is different from the pre-analysis treatment regimen.

As another example, in some embodiments, an individual has undergone treatment for epilepsy. Efficacy of the treatment is determined by detecting epileptic tissue (tissue affected by an epileptic seizure) in the individual, in the days, weeks, months, or years following treatment for epilepsy. Depending on the analysis of the efficacy of the treatment regimen, a recommendation is made for: a) discontinuation of treatment; b) an alteration of the treatment regimen, e.g., to increase the dose and/or frequency of treatment; or c) a treatment regimen that is different from the pre-analysis treatment regimen.

For example, in some embodiments, a subject method comprises: a) administering 2DG-functionalized MNPs at a first time to an individual having a disease, where the individual is being treated with a treatment regimen, where a first image is produced; b) administering to the individual a subject 2DG-functionalized MNP at a second time to the individual, where the second time is from about 1 day to about 1 year after the first time (e.g., where the second time is from about 1 day to about 2 days, from about 2 days to about 1 week, from about 1 week to about 2 weeks, from about 2 weeks to about 1 month, from about 1 month to about 2 months, from about 2 months to about 4 months, from about 4 months to about 6 months, from about 6 months to about 8 months, or from about 8 months to about 1 year, after the first time); and c) comparing the first and second images produced following the first and the second administrations. Further administrations at further time points are also contemplated. Where the second image, compared to the first image, indicates that the disease is progressing, medical personnel can recommend a different treatment regimen. Where the second image, compared to the first image, indicates that the disease is regressing, medical personnel can recommend that the treatment regimen be maintained.

In some embodiments, the disease progress is provided in a report. Thus, in some embodiments, a subject method further includes a step of preparing or generating a report that includes information regarding the disease progression and the treatment efficacy. For example, a subject method can further include a step of generating or outputting a report providing the results of a subject method, which report can be provided in the form of an electronic medium (e.g., an electronic display on a computer monitor), or in the form of a tangible medium (e.g., a report printed on paper or other tangible medium).

Subjects Suitable for Diagnosis

Subjects suitable for diagnosis (e.g., detection) with a subject 2DG-functionalized MNP include individuals who are suspected of having a particular disease, e.g., any of the above-mentioned diseases. For example, subjects suitable for diagnosis (e.g., detection) with a subject 2DG-functionalized MNP include individuals who are suspected of having a tumor. As another example, subjects suitable for diagnosis (e.g., detection) with a subject 2DG-functionalized MNP include individuals who are suspected of having had an epileptic seizure.

Subjects suitable for diagnosis (e.g., detection) with a subject 2DG-functionalized MNP include individuals who have been subjected to a diagnostic assay other than a subject diagnostic assay, where the results of the diagnostic assay of than a subject diagnostic assay are unclear, or need to be confirmed.

Subjects suitable for disease monitoring using a subject method include individuals who are undergoing treatment for a particular disease, e.g., any of the above-mentioned diseases. For example, subjects suitable for disease monitoring using a subject method include individuals who are undergoing treatment for cancer, where efficacy of treatment is monitored using a subject method.

Subjects Suitable for Treatment

Subjects suitable for treatment with a subject 2DG-functionalized MNP include individuals who have been diagnosed with a disease as discussed above.

Individuals in need of treatment include individuals having any of a variety of disorders, including, but not limited to, a neoplasm; Alzheimer's Disease; Huntington's Disease; Parkinson's Disease; amyotrophic lateral sclerosis, cardiac diseases; acute and chronic inflammatory diseases such as lupus and sarcoidosis; infectious diseases; vascular diseases; gastro-intestinal diseases; diseases of bone and bone marrow; congenital diseases; diabetes; obesity; kidney diseases; muscular diseases; diseases of fatty tissues; psychological, cognitive, and psychiatric disorders such as autism, depression, addiction, and schizophrenia; diseases of the pancreas; diseases of the urinary tract; diseases of reproductive organs; genetic diseases; diseases of, or associated with, impaired metabolic activity; diseases and disorders of the central nervous system; diseases of the lymphatic system; and pathologic, pathologic, or non-pathologic systemic and central changes associated with acute or chronic use of medications, medicinal substances, or illicit substances.

In some embodiments, the individual is one who has or who is suspected of having, a tumor. In some embodiments, the individual is one who has had, or who is suspected of having had, an epileptic seizure.

In some embodiments, the individual is one in whom administration (e.g., repeated administration) of a radioactive substance is contraindicated, e.g., a pediatric subject, a pregnant woman, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.v., intravenous(ly); i.m., intramuscular(ly); i.p., intraperitoneal(ly); s.c., subcutaneous(ly); and the like.

Example 1

Imaging 2DG MNPs in an Animal Model of Intracranial Tumors

2DG-functionalized MNPs were applied to an animal model of intracranial tumors. MRI scans were acquired. Uptake of 2DG-functionalized MNPs by intracranial tumors was shown; the 2DG-functionalized MNPs were able to clearly delineate tumor tissues from the surrounding normal (non-cancerous) brain tissues.

Methods

Tumor studies—Nude mice were injected intracranially with glioblastoma cell line U87Rluc (U87 glioblastoma cell line (ATCC HTB14) genetically modified to express luciferase). Dextran-coated magnetic nanoparticles were functionalized with 2DG. The 2DG moiety was attached to the dextran via the 6-carbon of 2DG. Baseline MR scans were obtained prior to injection with 2DG-MNP. Immediately after baseline scans, the mice were injected with 2DG-MNP (7 mg particles/kg body weight; 1.7 mg Fe/kg body weight) through the tail vein. Scans were obtained at 2 hours, 6 hours, and 24 hours post-MNP injection.

Results

The results are shown in FIGS. 1A-D, and FIGS. 2A-D.

FIG. 1a shows the MRI of a mouse with a glioblastoma prior to i.v. 2DG-MNP injection. FIGS. 1b-d show negative contrast enhancement in the glioblastoma at 2 hours, 6 hours, and 24 hours after i.v. injection of 2DG-MNP. Clearing is seen at 24 hours. Negative enhancement due to particle uptake as well as tumor delineation is clearly visible.

FIG. 2a shows MRI images in the resting mouse brain before i.v. 2DG-MNP injection, and FIGS. 2b-d show images obtained two hours, six hours, and 24 hours after i.v. injection of 2DG-MNP. Uniform uptake, displayed as negative enhancement, is observed especially in the thalamus and neocortex. Contrast cleared slowly over 24 hours.

Example 2

Imaging 2DG MNPs in an Animal Model of Epilepsy

Dextran-coated magnetic nanoparticles were functionalized with 2DG. The 2DG moiety was attached to the dextran via the 6-carbon of 2DG. 2DG-functionalized MNPs were applied to animal models of generalized epilepsy. MRI scans were acquired. It was shown that the brain distribution of 2DG-MNP in acute generalized epilepsy resembles that obtained by 2DG autoradiography.

Methods

Epilepsy studies—Baseline MRI scans were obtained from a healthy (naïve) Lewis rat. After the baseline scans, the rat was injected with pentanyl tetrazole (PTZ, 60 mg/kg, subcutaneous) to induce acute generalized seizures (Racine stage 2). The rat was then injected with 2DG-MNP (10 mg particles/kg body weight, intravenous, tail vein). Second scan was obtained 2 hours post MNP injection. After this scan, the rat was injected with an additional dose of PTZ (60 mg/kg, subcutaneous) to induce Racine Stage 4-5 seizures.

Results

Figure 3B:
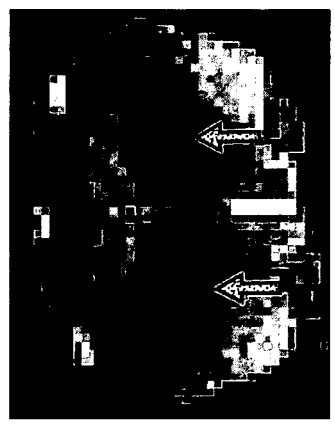
Figure 3A:
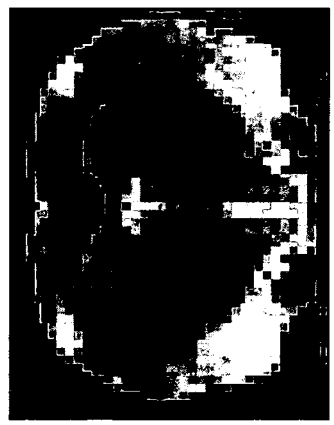
Figure 3E:
Figure 3D:
Figure 4A:
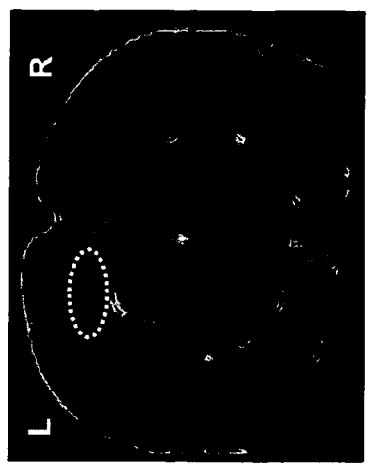
FIGS. 4A-F show 2DG-MNP contrast enhancement in an acute model of epilepsy induced by pilocarpine.
Figure 4B:
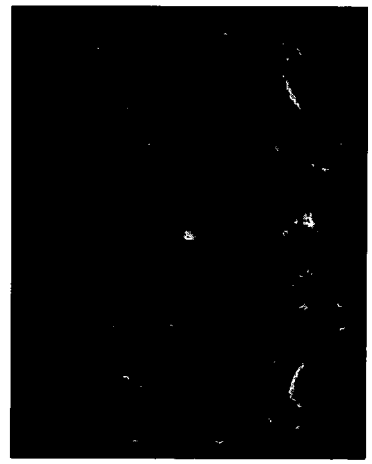
Figure 4C:
Figure 4D:
Figure 4E:
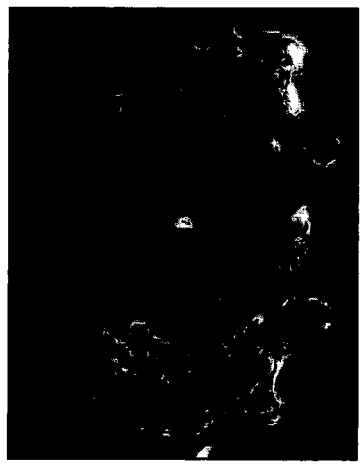
Figure 4F:
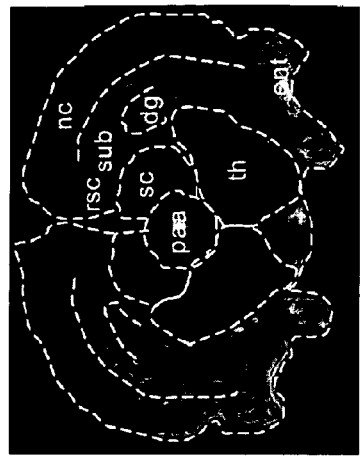

The results are shown in FIGS. 3A-E. FIG. 3A shows MR image of a naïve Lewis rat before 2DG-MNP injection and before induction of generalized epilepsy with PTZ. FIG. 3B shows distribution of particles in the neocortex, thalamus, and thalamic nuclei (blue arrows) after induction of low-grade seizures. FIG. 3C shows more contrast in thalamus and cortex in addition to uptake by hippocampus (yellow arrows). FIGS. 3D and 3E show the results of corresponding experiments with 2F-DG autoradiography. The images also show lack of appreciable uptake by entorhinal cortex in agreement with PET studies. There is striking agreement between the two techniques.

Example 3

Studies with Pilocarpine-Induced Seizures

A naïve Lewis rat was injected with intraperitoneally (IP) pilocarpine (PILO; 30 mg/kg). The rat was injected with 2DG-MNP (15 mg/kg, i.v. tail) after stage 4 seizures developed, and anesthetized with pentobarbital 10 minutes thereafter. MRI images were acquired. The data are shown in FIGS. 4A-F.

FIGS. 4A-F. Panel a) shows the MR images of a naïve Lewis rat. Panels b), c), d), and e) show pattern of 2DG-MNP uptake, 1, 2, 2.5, and 3 hours, respectively after particle injection. The signal intensity in subiculum, dentate gyrus, and retrosplenial cortex, white ellipse, was measured and showed increased (negative) signal enhancement of about 22% in this period. Negative signal enhancement in the peri-thalamic ventricles also indicates the particles have crossed the BBB. Panel f) shows the approximate location of the slice on Paxinos atlas. Dashed lines outline some of the brain areas. Abbreviations are: nc—neocortex; rsc—retrosplenial cortex; sub—subiculum; dg—dentate gyrus; sc—superior colliculus; paa—periaquaductal areas; th—thalamus; ent—entorhinal cortex.

Example 4

Studies with Kainic Acid-Induced Seizures

A Lewis rat was given chronic kainic acid (KA) treatment. The rat was injected with 2DG-MNP (15 mg/kg, i.v. tail) after stage 4 seizures developed, and anesthetized with pentobarbital 10 minutes thereafter.

FIG. 5a) shows the MR image of a chronic KA treated rat. This rat showed presence of seizures on video monitoring. FIGS. 5b) and 5c) show the uniform interictal distribution of contrast enhancement in consecutive MRI slices 1 hour after injection (15 mg/kg, i.v. tail) with 2DG-MNP particles. No cerebral uptake or increased contrast enhancement is visible, showing that the ligand is active in producing contrast enhancement.

Figure 6A:
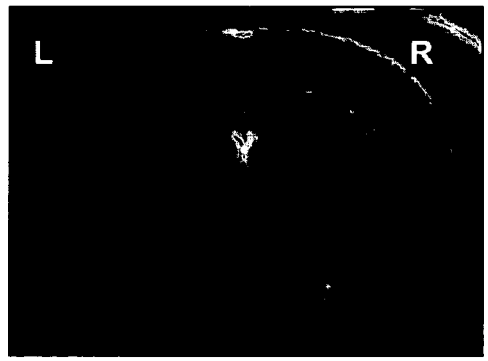
FIGS. 6A and B depict results showing that unconjugated MNP does not produce contrast enhancement in the same kainic acid treated animal as in FIG. 5 in the interictal period.
Figure 6B:
Figure 7:
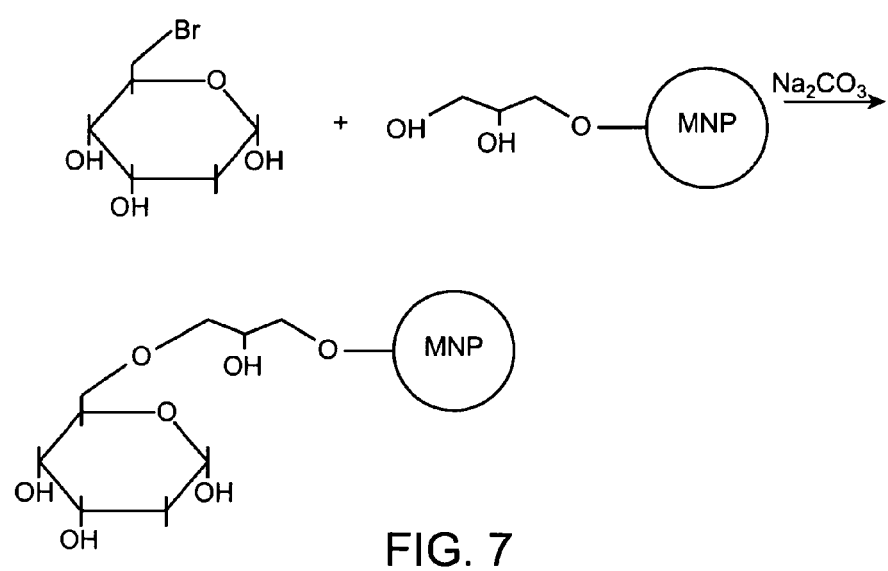
FIG. 7 depicts conjugation of 2DG-MNP at the 6-carbon (replacement of 6 hydroxyl group) site.
Figure 8:
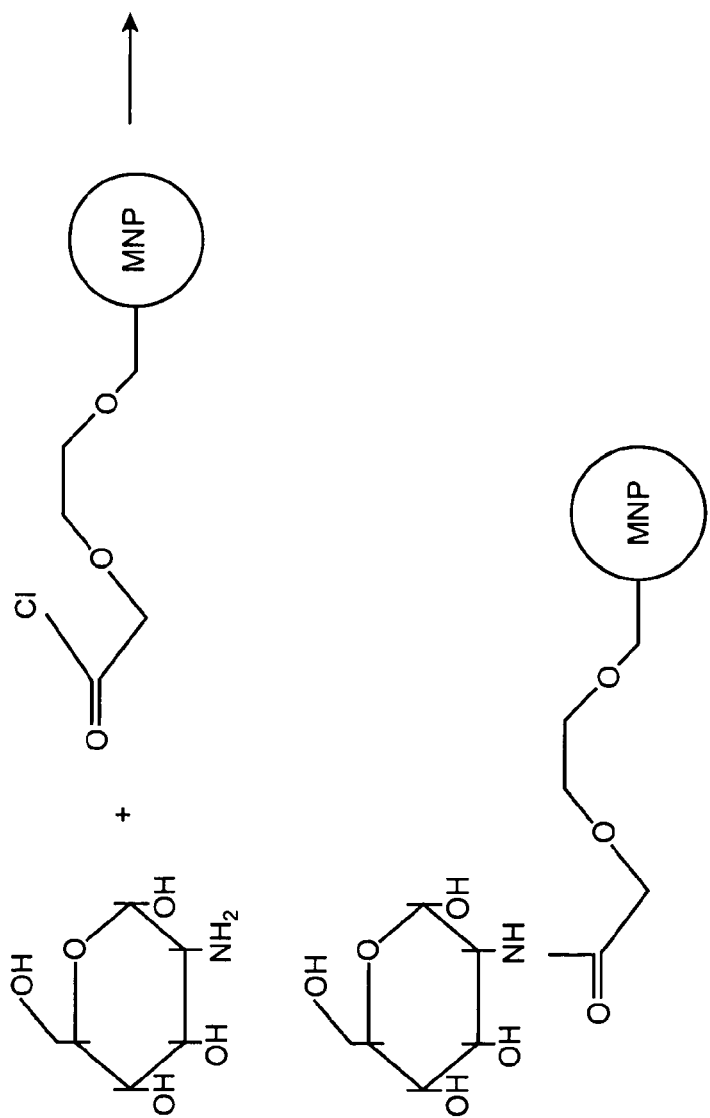
FIG. 8 depicts conjugation of 2DG-MNP at the 2-carbon site.

FIGS. 6a) and b) show the MR images of the KA rat used in FIG. 5, before and after, respectively, injection with unconjugated (plain) MNPs (15 mg/kg, i.v. tail). The only difference between the plain and 2DG-MNP particles is the presence of 2DG. No cerebral uptake or increased contrast enhancement is visible; this shows that the ligand is active in producing contrast enhancement.

Example 5

Comparison of 2DG-MNP Imaging and Gadolinium Imaging

Brains of mice with medulloblastoma were imaged. Magnetic resonance (MR) images were obtained with multiple slice multiple echo (MSME) T2 scan (TR=6000 ms, TE 10-60 ms in steps of 10 ms, FOV=35 mm, slice thickness=1 mm, zero spacing) on a 7T magnet (Bruker Biospin, Germany). Mice were administered with: 1) no contrast agent; 2) gadolinium; or 3) 2DG-MNP.

Figure 9A:
FIGS. 9A and 9B depict: 9A) a baseline image of the mouse brain with a large medulloblastoma; and 9B) a T2 reconstruction of the image in 9A.
Figure 9B:
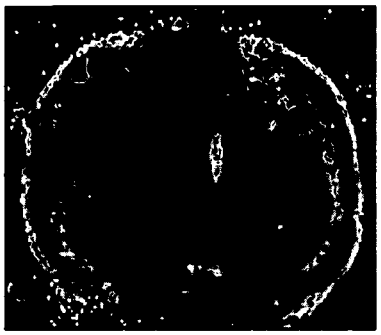

FIGS. 9A and 9B show brain images from mice administered no contrast agent. FIG. 9A shows the baseline image of the mouse brain with a large medulloblastoma. FIG. 9B shows the T2 reconstruction of the image in FIG. 9A. The T2 value of the tumor was measured at 57.7±2.3 ms.

Figure 10A:
FIGS. 10A and 10B depict: 10A) a magnetic resonance imaging (MRI) scan of the mouse brain with a large medulloblastoma, after injection of 100 μl of gadolinium chelate; and 10B) a T2 reconstruction of the image in 10A.
Figure 10B:

FIGS. 10A and 10B show brain images from mice administered with gadolinium. FIG. 10A shows the MRI scan of the same mouse after injection with 100 μl of Gadolinium chelate (Gado). FIG. 10B shows the T2 reconstruction of the image in FIG. 10A. The T2 value of the tumor was measured at 51.3±2.1 ms.

Figure 11A:
FIGS. 11A and 11B depict: 11A) an MRI scan of the mouse brain with a large medulloblastoma, after injection with 100 μl of 2DG-MNP; and 11B) a T2 reconstruction of the image in 11A.
Figure 11B:
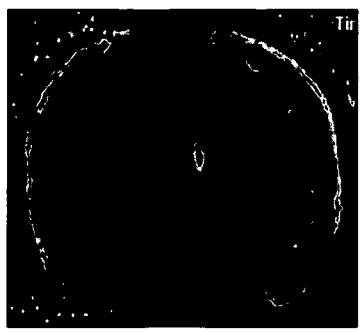

FIGS. 11A and 11B brain images from mice administered with 2DG-MNP. FIG. 11A shows the MRI scan of the same mouse after injection with 100 µl of 2DG-MNP. FIG. 11B shows the T2 reconstruction of the image in FIG. 11A. The T2 value of the tumor was measured at 48.2±2.5 ms.

These data show that 2DG-MNP decreases tissue T2 values more that Gado, and that 2DG-MNP reveal more tumor tissue that Gado. Furthermore, 2DG-MNP can be used to stage and grade tumors pre- and post-treatment, whereas Gado has limited utility for such applications.

Example 6

Imaging Functional Brain Activity

Functional brain activity was imaged in a resting naïve rat, in a rat following electrical stimulation of the left upper lip in the whisker area, and in a rat following electrical stimulation of the left forepaw.

Figure 12A:
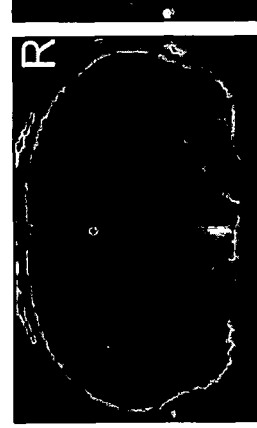
FIGS. 12A-D depict images of a normal and resting mouse brain before (FIG. 12A) and 2 hours (FIG. 12B), 6 hours (FIG. 12C), and 24 hours (FIG. 12D) after injection with 2DG-MNP.
Figure 12B:
Figure 12C:
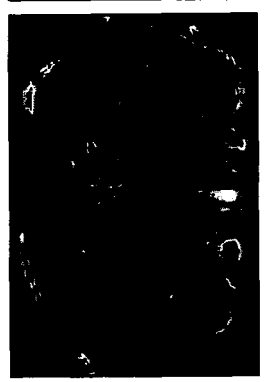
Figure 12D:
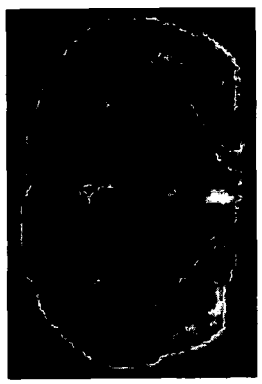
Figure 12E:
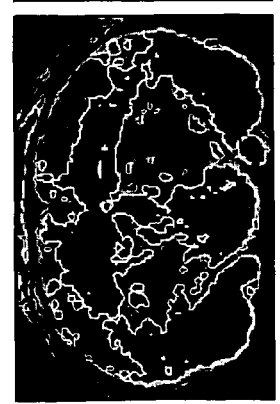
FIG. 12E shows an overlay of the images in 12A and 12B.
Figure 12F:
FIG. 12F depicts a $^{14}$C-2DG autoradiograph of a naïve mouse brain.

FIGS. 12A-F show images in the resting naïve rat. FIG. 12A shows an MR image in the naïve mouse before i.v. 2DG-MNP injection. FIGS. 12B, 12C, and 12D show images obtained two hours, six hours, and 24 hours, respectively, after i.v. injection of 2DG-MNP (15 mg/kg, i.v. via the tail vein). Uniform uptake, displayed as negative enhancement, is observed especially in the thalamus and neocortex. Contrast cleared after approximately 24 hours. Note that the columnar structure of the neocortex is visible on 2DG-MNP MRI images. FIG. 12E shows the overlay of thresholded quantitative densitometry in FIG. 12B compared to FIG. 12A; this comparison showed as four-fold increase in cortical contrast. FIG. 12F shows the $^{14}C$-2DG autoradiograph of a naïve mouse brain; the distributions of contrasts are very similar.

Figure 13C:
FIGS. 13A-F depict images of a naïve rat brain, and rat brain after electrical stimulation of the left whisker area.
Figure 13B:
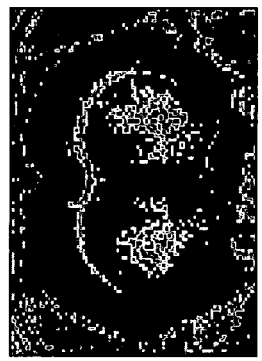
Figure 13E:
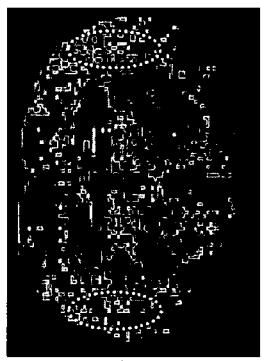
Figure 13A:
Figure 13D:
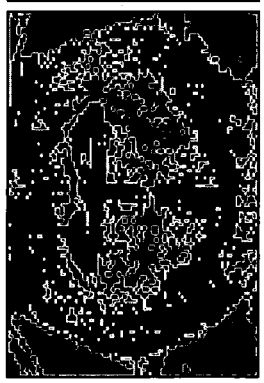
Figure 13F:

FIGS. 13A-F show that MRI detects localized 2DG-MNP concentration in the barrel area of the right somatosensory cortex during electrical stimulation of the left upper lip in the whisker area. 2DG-MNP was injected i.v. (bolus, 10 sec) during 45 minutes of stimulation. The prestimulation, preinjection (baseline) image is shown in FIG. 13A; the corresponding quantitative T2 map in FIG. 13B shows uniform cortical T2 values. The MR image shown in FIG. 13C was obtained 90 minutes after injection with 2DG-MNP (3 mg Fe/kg, i.v.) and 45 minutes after stop of the stimulation. Magnification of the right barrel cortex shows corresponding cortical columns. FIG. 13D is a quantitative T2 map of the MR image presented in FIG. 13C. FIG. 13E is a superimposition of the post-stimulation T2 map and the post-stimulation MRI. The T2 values of the right and left cortex (white ellipses) were measured at 56.5±4.2 ms and 70±5.4 ms, respectively. The asymmetry of the T2 map in these images shows contrast enhancement of the right barrel cortex at the level of mid-hippocampus; these results are consistent with $^{14}C$-autoradiographic imaging of vibrissae stimulation as shown in FIG. 13F.

FIGS. 14A-D illustrate MR images from a similar experiment in the same animal as in FIG. 13A-F, showing 2DG-MNP concentration in the front paw area of the right somatosensory cortex with 70 minutes of stimulation of the left front paw. FIG. 14A is a prestimulation preinjection (baseline) image. FIG. 14B shows a quantitative T2 map of the baseline scan presented in FIG. 14A. FIG. 14C shows an MR scan of the same rat after injection with 2DG-MNP (3 mg Fe/kg) and electrical stimulation of the left forepaw for 70 minutes; magnification of the paw projection area of the somatosensory neocortex shows visible cortical columns, while 5d image was obtained 120 minutes after IV 2DG-MNP injection.

Example 7

Imaging Seizures

FIGS. 15A and 15B show two consecutive baseline interictal MR image slices, at the mid-hippocampus level, from a rat with spontaneous seizures after PILO induced status epilepticus. FIGS. 15C and 15D show the corresponding contrast enhancement with 2DG-MNP following PTZ induced focal seizures (Racine stage 2); contrast enhancement is predominantly in the entorhinal cortex (EC), bilaterally. The rat was subsequently implanted with intracranial EEG electrodes; FIG. 15E shows the intracranial EEG measurements of the same rat during a PTZ-induced seizure identical in semiology to those produced prior to the MR scans. EEG showed seizure onset in the right (R)EC shortly before left (L)EC followed by delayed seizure activity in the left hippocampus (LHip).

The results of the studies described above demonstrate that 2DG-MNP can be used to delineate changes in local neuronal function on MRI: 1) The MRI patterns observed before and after 2DG-MNP injection indicate that these paramagnetic particles cross the blood-brain barrier in the normal mouse, with focal stimulation in the rat, in the glioblastoma mouse, and during PTZ- and PILO-induced seizures in the rat, and that the clearance of negative enhancement is consistent with that of cerebral metabolism measured by 2-fluoro-2-deoxy-D-glucose-positron emission tomography (FDG-PET) and 2DG autoradiography. 2) The pattern of 2DG-MNP uptake in the naïve mouse is consistent with that of known normal cerebral neuronal activity; the pattern of uptake with focal stimulation conforms to the known patterns of 2DG-MNP uptake in the rat during PTZ- and PILO-induced generalized and focal seizures is concentrated in hippocampus, cortex, and thalamus, in a manner similar to that obtained with generalized and focal kindled seizures in the rat with 2DG autoradiography, and also observed with generalized and focal seizures in mesial temporal lobe epilepsy (MTLE) patients using FDG-PET.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition comprising: a) a functionalized magnetic nanoparticle (MNP) comprising at least one functional moiety, wherein the at least one functional moiety comprises 2-deoxyglucose, and wherein the functionalized MNP exhibits differential affinity and/or metabolic uptake into a mammalian tissue; wherein the magnetic nanoparticle comprises a magnetic core particle and a biocompatible substrate, and wherein the 2DG is linked to the biocompatible substrate, wherein the 2DG is linked to the biocompatible substrate via the 6-position —OH, oxygen of 2DG; and b) a pharmaceutically acceptable carrier.

2. The composition of claim 1, wherein the biocompatible substrate is dextran, an iron-dextran complex, a polysaccharide, polyethylene glycol, a polyethylene oxide, starch, a phospholipid, a poloxamer, a poloxamine, a silicone, a polyvinyl alcohol, or albumin.

3. The composition of claim 1, wherein the functionalized MNP has a diameter of from about 10 nm to about 300 nm.

4. The composition of claim 1, wherein said functionalized magnetic nanoparticle is capable, when injected into the bloodstream of a mammalian subject, of crossing the blood-brain barrier of said subject.

5. The composition of claim 1, wherein the tissue is a diseased tissue.

6. The composition of claim 5, wherein the level of metabolic uptake of the functionalized MNP by the diseased tissue is less than the level of metabolic uptake of the functionalized MNP by normal tissue.

7. The composition of claim 6, wherein the diseased tissue is a plaque associated with Alzheimer's Disease, a tissue affected by Huntington's Disease, a tissue affected by Parkinson's Disease, a diseased cardiac tissue, a tissue affected by amyotrophic lateral sclerosis.

8. The composition of claim 5, wherein the level of metabolic uptake of the functionalized MNP by the diseased tissue is greater than the level of metabolic uptake of the functionalized MNP by normal tissue.

9. The composition of claim 8, wherein the tissue is a cancerous tissue.

10. The composition of claim 8, wherein the tissue is an epileptigenic tissue.

11. The composition of claim 1, wherein the functionalize MNP comprises at least a second functional moiety.

12. The composition of claim 11, wherein the second functional moiety comprises a therapeutic agent.

13. A method of detecting a tissue in a living mammalian subject, the method comprising
    a) administering to a mammalian subject a composition according to claim 1, wherein the functionalized MNP exhibits differential affinity for, and/or metabolic uptake into, a tissue in the mammalian subject; and
    b) detecting the presence of the functionalized MNP in association with the tissue.

14. The method of claim 8, wherein the tissue is a diseased tissue.

15. The method of claim 14, wherein the level of metabolic uptake of the functionalized MNP by the diseased tissue is less than the level of metabolic uptake of the functionalized MNP by normal tissue.

16. The method of claim 15, wherein the diseased tissue is a plaque associated with Alzheimer's Disease, a tissue affected by Huntington's Disease, a tissue affected by Parkinson's Disease, a diseased cardiac tissue, and a tissue affected by amyotrophic lateral sclerosis.

17. The method of claim 14, wherein the level of metabolic uptake of the functionalized MNP by the diseased tissue is greater than the level of metabolic uptake of the functionalized MNP by normal tissue.

18. The method of claim 17, wherein the tissue is a cancerous tissue.

19. The method of claim 17, wherein the tissue is an epileptic lesion.

20. The method of claim 13, wherein the functionalized MNP further comprises at least a second functional moiety.

21. The method of claim 20, wherein the second functional moiety comprises a therapeutic agent.

22. The method of claim 13, wherein said detecting comprises magnetic resonance imaging.

23. The method of claim 13, wherein said detecting comprises computed tomography.

24. A method of treating a disease in an individual, the method comprising administering a composition according to claim 12 to the individual, wherein the functionalized MNP exhibits differential affinity for, and/or differential metabolic uptake into, a diseased tissue associated with the disease, and wherein the therapeutic agent treats the disease.

25. The method of claim 24, wherein the diseased tissue is an epileptic lesion, and the therapeutic agent is an anti-seizure agent.

26. The method of claim 24, wherein the diseased tissue is a tissue affected by Parkinson's Disease, and wherein the therapeutic agent is L-DOPA.

27. The method of claim 26, wherein the diseased tissue is a tissue affected by Alzheimer's Disease, and wherein the therapeutic agent is donepezil HCl, rivastigmine, galantamine, memantine, or tacrine.

28. The method of claim 24, wherein the diseased tissue is a cancerous tissue, and the therapeutic agent is an anti-cancer agent.

29. A method of predicting the likelihood that an individual will develop a disease, the method comprising:
    a) administering to the individual a composition according to claim 1, wherein the functionalized MNP exhibits differential affinity for, and/or metabolic uptake into, a tissue in the mammalian subject; and
    b) using an imaging method to the presence of the functionalized MNP in association with the tissue;
    c) using the results of (b) to determine the likelihood that the individual will develop a disease, thereby generating a disease likelihood assessment.

30. The method of claim 29, further comprising preparing a report that includes the disease likelihood assessment.

31. The method of claim 29, further comprising recommending a treatment regimen based on the disease likelihood assessment.

32. The composition of claim 1, wherein the mammalian tissue is brain tissue.

* * * * *

UNITED STATES PATENT AND TRADEMARK OFFICE
CERTIFICATE OF CORRECTION

| | | |
|---|---|---|
| PATENT NO. | : 8,445,021 B2 | Page 1 of 1 |
| APPLICATION NO. | : 12/934044 | |
| DATED | : May 21, 2013 | |
| INVENTOR(S) | : Akhtari et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
Twenty-seventh Day of January, 2015

Michelle K. Lee
*Deputy Director of the United States Patent and Trademark Office*